US011857212B2

(12) United States Patent
Capelli et al.

(10) Patent No.: US 11,857,212 B2
(45) Date of Patent: Jan. 2, 2024

(54) RAPID PULSE ELECTROHYDRAULIC (EH) SHOCKWAVE GENERATOR APPARATUS WITH IMPROVED ELECTRODE LIFETIME

(71) Applicant: Soliton, Inc., Houston, TX (US)

(72) Inventors: Christopher C. Capelli, Houston, TX (US); Michael Kishinevsky, Houston, TX (US); Daniel Masse, Houston, TX (US); John Summerson, Houston, TX (US); David Robertson, Houston, TX (US); Walter Klemp, Houston, TX (US); Robert Crowley, Houston, TX (US)

(73) Assignee: Soliton, Inc., Houston, TX (US)

(*) Notice: Subject to any disclaimer, the term of this patent is extended or adjusted under 35 U.S.C. 154(b) by 673 days.

(21) Appl. No.: 16/319,509

(22) PCT Filed: Jul. 14, 2017

(86) PCT No.: PCT/US2017/042122
§ 371 (c)(1),
(2) Date: Jan. 22, 2019

(87) PCT Pub. No.: WO2018/017414
PCT Pub. Date: Jan. 25, 2018

(65) Prior Publication Data
US 2020/0222068 A1 Jul. 16, 2020

Related U.S. Application Data

(60) Provisional application No. 62/365,099, filed on Jul. 21, 2016.

(51) Int. Cl.
*A61B 17/225* (2006.01)
*A61B 17/22* (2006.01)
(Continued)

(52) U.S. Cl.
CPC ...... *A61B 17/225* (2013.01); *A61B 17/22004* (2013.01); *A61B 2017/22025* (2013.01);
(Continued)

(58) Field of Classification Search
CPC ............ A61B 17/225; A61B 17/22004; A61B 2017/22025; A61B 2017/22027; A61H 23/008; A61N 7/00
See application file for complete search history.

(56) References Cited

U.S. PATENT DOCUMENTS 3,234,429 A * 2/1966 Schrom ............... B21D 26/12
315/111.01
3,364,708 A * 1/1968 Padberg, Jr. ........... G01V 1/157
72/56
(Continued)

FOREIGN PATENT DOCUMENTS

CN 1245410 2/2000
CN 101028525 9/2007
(Continued)

OTHER PUBLICATIONS

Baumler, et al., "Q-Switch Laser and Tattoo Pigments: First Results of the Chemical and Photophysical Analysis of 41 Compounds," *Lasers in Surgery and Medicine*, 26:13-21, 2000.
(Continued)

*Primary Examiner* — Christopher Koharski
*Assistant Examiner* — Sean A Frith
(74) *Attorney, Agent, or Firm* — Mintz, Levin, Cohn, Ferris, Glovsky and Popeo, P.C.

(57) ABSTRACT

Apparatuses, capacitor arrays, and methods for generating therapeutic compressed acoustic waves (e.g., shock waves). In the apparatuses and at least some of the methods, a plurality of electrodes can disposed in a chamber that is
(Continued)

defined by a housing and configured to be filled with liquid, and a plurality of capacitors can be electrically connected to the electrodes and can be carried by (e.g., physically coupled to) the housing. Voltage pulses can be applied simultaneously to the plurality of electrodes (e.g., to begin to vaporize and ionize portions of the liquid to provide at least one inter-electrode conductive path between the plurality of electrodes) and to the capacitors to charge the plurality of capacitors). The plurality of capacitors can be configured to, upon reaching a threshold charge, discharge to the plurality of electrodes (e.g., to generate one or more arcs along the one or more inter-electrode conductive paths to vaporize additional portions of the liquid and generate one or more acoustic shock waves). In the capacitor arrays, a plurality of capacitors can be coupled to the one or more circuit boards with a first portion of the capacitors arranged in a first pattern defined by a plurality of capacitor sets, a second portion of the plurality of capacitors can be arranged in a second pattern defined by a plurality of capacitor sets, with the sets defining the first pattern connected in parallel, the sets defining the second pattern connected in parallel, and the circuit board(s) can be configured to be coupled to an electrode such that the electrode is in electrical communication with the capacitors and is fixed in at least two degrees of freedom relative to the one or more circuit boards.

20 Claims, 14 Drawing Sheets

(51) Int. Cl.
*A61H 23/00* (2006.01)
*A61N 7/00* (2006.01)

(52) U.S. Cl.
CPC .. *A61B 2017/22027* (2013.01); *A61H 23/008* (2013.01); *A61N 7/00* (2013.01)

(56) References Cited

U.S. PATENT DOCUMENTS

| | | | |
|---|---|---|---|
| 3,475,646 A * | 10/1969 | Chapman | H01T 1/00 315/59 |
| 3,604,641 A | 9/1971 | Wilson et al. | |
| 3,613,069 A | 10/1971 | Cary | |
| 3,735,764 A | 5/1973 | Balev et al. | |
| 3,769,963 A | 11/1973 | Goldman et al. | |
| 3,942,531 A | 3/1976 | Hoff et al. | |
| 3,983,749 A * | 10/1976 | Fletcher | G10K 15/06 73/147 |
| 4,005,314 A | 1/1977 | Zinn | |
| 4,311,147 A | 1/1982 | Hausler | |
| 4,715,376 A | 12/1987 | Nowacki et al. | |
| 4,858,597 A | 8/1989 | Kurtze et al. | |
| 4,896,673 A | 1/1990 | Rose et al. | |
| 4,905,671 A | 3/1990 | Senge et al. | |
| 4,928,671 A | 5/1990 | Reichenberger et al. | |
| 4,955,143 A | 9/1990 | Hagelauer | |
| 4,962,752 A | 10/1990 | Reichenberger et al. | |
| 4,979,501 A | 12/1990 | Valchanov et al. | |
| 5,009,232 A | 4/1991 | Hassler et al. | |
| 5,015,929 A | 5/1991 | Cathignol et al. | |
| 5,071,422 A | 12/1991 | Watson et al. | |
| 5,146,912 A | 9/1992 | Eizenhoefer | |
| 5,149,406 A | 9/1992 | Mullen et al. | |
| 5,150,713 A | 9/1992 | Okazaki | |
| 5,193,527 A | 3/1993 | Schafer | |
| 5,195,508 A | 3/1993 | Muller et al. | |
| 5,204,820 A | 4/1993 | Strobel et al. | |
| 5,231,976 A | 8/1993 | Wiksell | |
| 5,240,005 A | 8/1993 | Viebach | |
| 5,245,988 A | 9/1993 | Einars et al. | |
| 5,251,614 A | 10/1993 | Cathignol et al. | |
| 5,259,368 A * | 11/1993 | Wiksell | G10K 15/06 367/147 |
| 5,269,292 A | 12/1993 | Granz et al. | |
| 5,284,143 A | 2/1994 | Rattner | |
| 5,304,170 A | 4/1994 | Green | |
| 5,304,207 A | 4/1994 | Stromer | |
| 5,327,890 A | 7/1994 | Matura et al. | |
| 5,360,447 A | 11/1994 | Koop | |
| 5,374,236 A | 12/1994 | Hassler | |
| 5,393,296 A | 2/1995 | Rattner | |
| 5,409,446 A | 4/1995 | Rattner | |
| 5,419,327 A | 5/1995 | Rohwedder et al. | |
| 5,423,803 A | 6/1995 | Tankovich et al. | |
| 5,435,304 A | 7/1995 | Oppelt et al. | |
| 5,458,652 A | 10/1995 | Uebelacker | |
| 5,509,200 A | 4/1996 | Frankeny et al. | |
| 5,529,572 A | 6/1996 | Spector | |
| 5,595,178 A | 1/1997 | Voss et al. | |
| 5,618,275 A | 4/1997 | Bock | |
| 5,658,239 A | 8/1997 | Delmenico | |
| 5,675,495 A | 10/1997 | Biermann et al. | |
| 5,676,159 A | 10/1997 | Navis | |
| 5,709,676 A | 1/1998 | Alt | |
| 5,722,411 A | 3/1998 | Suzuki et al. | |
| 5,737,462 A | 4/1998 | Whitehouse et al. | |
| 5,743,862 A | 4/1998 | Izumi | |
| 5,790,305 A | 8/1998 | Marcellin-Dibon et al. | |
| 5,827,204 A | 10/1998 | Grandia et al. | |
| 6,013,122 A | 1/2000 | Klitzman et al. | |
| 6,036,661 A | 3/2000 | Schwarze et al. | |
| 6,039,694 A | 3/2000 | Larson et al. | |
| 6,058,932 A | 5/2000 | Hughes | |
| 6,080,119 A | 6/2000 | Schwarze et al. | |
| 6,096,029 A | 8/2000 | O'Donnell, Jr. | |
| 6,113,559 A | 9/2000 | Klopotek | |
| 6,113,560 A | 9/2000 | Simnacher | |
| 6,123,679 A | 9/2000 | Lafaut et al. | |
| 6,176,839 B1 | 1/2001 | Deluis et al. | |
| 6,186,963 B1 | 2/2001 | Schwarze et al. | |
| 6,210,329 B1 | 4/2001 | Christmas et al. | |
| 6,217,531 B1 | 4/2001 | Reitmajer | |
| 6,309,355 B1 | 10/2001 | Cain et al. | |
| 6,325,769 B1 | 12/2001 | Klopotek | |
| 6,350,245 B1 | 2/2002 | Cimino | |
| 6,368,929 B1 | 4/2002 | Hill et al. | |
| 6,390,995 B1 | 5/2002 | Ogden et al. | |
| 6,450,979 B1 | 9/2002 | Miwa et al. | |
| 6,454,713 B1 | 9/2002 | Ishibashi et al. | |
| 6,487,447 B1 | 11/2002 | Weimann et al. | |
| 6,491,685 B2 | 12/2002 | Visuri | |
| 6,500,141 B1 | 12/2002 | Irion et al. | |
| 6,515,842 B1 * | 2/2003 | Hayworth | H01C 7/10 361/303 |
| 6,519,376 B2 | 2/2003 | Biagi et al. | |
| 6,551,308 B1 | 4/2003 | Muller et al. | |
| 6,666,834 B2 | 12/2003 | Restle et al. | |
| 6,755,821 B1 | 6/2004 | Fry | |
| 6,800,122 B2 | 10/2004 | Anderson et al. | |
| 6,905,467 B2 | 6/2005 | Bradley | |
| 6,942,663 B2 | 9/2005 | Vargas et al. | |
| 6,948,843 B2 | 9/2005 | Laugharn et al. | |
| 6,972,116 B2 | 12/2005 | Brill et al. | |
| 7,189,209 B1 | 3/2007 | Ogden et al. | |
| 7,250,047 B2 | 7/2007 | Anderson et al. | |
| 7,311,678 B2 | 12/2007 | Spector | |
| 7,364,554 B2 | 4/2008 | Bolze et al. | |
| 7,405,510 B2 | 6/2008 | Kaminski et al. | |
| 7,470,240 B2 | 12/2008 | Schultheiss et al. | |
| 7,507,213 B2 | 3/2009 | Schultheiss et al. | |
| 7,588,547 B2 | 9/2009 | Deem et al. | |
| 7,867,178 B2 | 1/2011 | Shiuiacher | |
| 7,985,189 B1 | 7/2011 | Ogden et al. | |
| 7,988,631 B2 | 8/2011 | Bohris | |
| 8,057,408 B2 | 11/2011 | Cain et al. | |
| 8,088,073 B2 | 1/2012 | Simnacher et al. | |
| 8,092,401 B2 | 1/2012 | Schultheiss | |
| 8,102,734 B2 | 1/2012 | Sliwa et al. | |

(56) References Cited

U.S. PATENT DOCUMENTS

| | | |
|---|---|---|
| 8,235,899 B2 | 8/2012 | Hashiba |
| 8,257,282 B2 | 9/2012 | Uebelacker et al. |
| 8,298,162 B2 | 10/2012 | Del Giglio |
| 8,323,220 B2 | 12/2012 | Babaev |
| 8,343,420 B2 | 1/2013 | Cioanta et al. |
| 8,357,095 B2 | 1/2013 | Anderson et al. |
| 8,672,721 B2 | 3/2014 | Camilli |
| 8,684,970 B1 | 4/2014 | Koyfman et al. |
| 2002/0009015 A1 | 1/2002 | Laugharn et al. |
| 2002/0193831 A1 | 12/2002 | Smith |
| 2003/0167964 A1 | 9/2003 | Anderson et al. |
| 2003/0233045 A1 | 12/2003 | Vaezy |
| 2004/0006288 A1 | 1/2004 | Spector et al. |
| 2004/0181219 A1 | 9/2004 | Goble et al. |
| 2005/0015023 A1 | 1/2005 | Ein-Gal |
| 2005/0049543 A1 | 3/2005 | Anderson et al. |
| 2005/0150830 A1 | 7/2005 | Laugharn et al. |
| 2006/0036168 A1 | 2/2006 | Liang et al. |
| 2006/0064082 A1 | 3/2006 | Bonutti |
| 2006/0094988 A1 | 5/2006 | Tosaya et al. |
| 2006/0158956 A1 | 7/2006 | Laugharn et al. |
| 2006/0173388 A1 | 8/2006 | Ginter et al. |
| 2006/0184071 A1 | 8/2006 | Klopotek |
| 2006/0200116 A1 | 9/2006 | Ferren et al. |
| 2006/0211958 A1 | 9/2006 | Rosenberg et al. |
| 2007/0016112 A1 | 1/2007 | Schultheiss et al. |
| 2007/0038060 A1 | 2/2007 | Cerwin et al. |
| 2007/0049829 A1 | 3/2007 | Kaminski et al. |
| 2007/0055157 A1 | 3/2007 | Bohris |
| 2007/0055180 A1 | 3/2007 | Deem et al. |
| 2007/0065420 A1 | 3/2007 | Johnson |
| 2007/0135755 A1 | 6/2007 | Bernabei et al. |
| 2007/0198068 A1 | 8/2007 | Chan et al. |
| 2007/0219760 A1 | 9/2007 | Yang et al. |
| 2007/0239072 A1 | 10/2007 | Schultheiss |
| 2007/0239082 A1 | 10/2007 | Schultheiss et al. |
| 2007/0239084 A1 | 10/2007 | Voss |
| 2007/0249939 A1 | 10/2007 | Gerbi et al. |
| 2008/0009774 A1 | 1/2008 | Capelli et al. |
| 2008/0009885 A1 | 1/2008 | Del Giglio |
| 2008/0021447 A1 | 1/2008 | Davison et al. |
| 2008/0071198 A1 | 3/2008 | Ogden et al. |
| 2008/0107744 A1 | 5/2008 | Chu |
| 2008/0132810 A1 | 6/2008 | Scoseria et al. |
| 2008/0146971 A1 | 6/2008 | Uebelacker et al. |
| 2008/0154157 A1 | 6/2008 | Altshuler et al. |
| 2008/0183200 A1 | 7/2008 | Babaev |
| 2008/0194967 A1 | 8/2008 | Sliwa et al. |
| 2008/0195003 A1 | 8/2008 | Sliwa et al. |
| 2008/0262483 A1 | 10/2008 | Capelli et al. |
| 2008/0269163 A1 | 10/2008 | Sostaric |
| 2008/0269608 A1 | 10/2008 | Anderson et al. |
| 2008/0319356 A1 | 12/2008 | Cain et al. |
| 2009/0018472 A1 | 1/2009 | Soltani et al. |
| 2009/0062644 A1 | 3/2009 | McMorrow et al. |
| 2009/0275832 A1 | 11/2009 | Gelbart et al. |
| 2010/0049098 A1 | 2/2010 | Shalgi et al. |
| 2010/0076349 A1 | 3/2010 | Babaev |
| 2010/0082019 A1 | 4/2010 | Neev |
| 2010/0087899 A1 | 4/2010 | Erez et al. |
| 2010/0168575 A1 | 7/2010 | Hashiba |
| 2010/0204617 A1 | 8/2010 | Ben-Ezra |
| 2010/0208467 A1 | 8/2010 | Dross |
| 2010/0249768 A1 | 9/2010 | Avramenko et al. |
| 2010/0274161 A1 | 10/2010 | Azhari et al. |
| 2010/0280420 A1 | 11/2010 | Barthe et al. |
| 2010/0331741 A9 | 12/2010 | Cioanta et al. |
| 2011/0034832 A1 | 2/2011 | Cioanta et al. |
| 2011/0087157 A1 | 4/2011 | Cioanta et al. |
| 2011/0319793 A1 | 12/2011 | Hynynen |
| 2012/0157892 A1 | 6/2012 | Reitmajer et al. |
| 2012/0167174 A1 | 6/2012 | Saxena et al. |
| 2012/0253240 A1 | 10/2012 | Uebelacker et al. |
| 2012/0253416 A1 | 10/2012 | Erez et al. |
| 2012/0271169 A1 | 10/2012 | Coussios et al. |
| 2012/0310232 A1 | 12/2012 | Erez |
| 2012/0323147 A1 | 12/2012 | Scheirer |
| 2012/0330288 A1 | 12/2012 | Clementi et al. |
| 2013/0018287 A1 | 1/2013 | Capelli |
| 2013/0046179 A1 | 2/2013 | Humayun |
| 2013/0046207 A1 | 2/2013 | Capelli |
| 2013/0345600 A1 | 12/2013 | Katragadda et al. |
| 2014/0005576 A1 | 1/2014 | Adams et al. |
| 2014/0094718 A1 | 4/2014 | Feldman |
| 2014/0228820 A1 | 8/2014 | Blaskowski et al. |
| 2014/0243715 A1 | 8/2014 | Cioanta et al. |
| 2014/0243847 A1 | 8/2014 | Hakala et al. |
| 2014/0257144 A1* | 9/2014 | Capelli .............. A61B 17/2251 |
| | | 601/2 |
| 2014/0276693 A1 | 9/2014 | Altshuler et al. |
| 2014/0276722 A1 | 9/2014 | Parihar et al. |
| 2014/0277219 A1 | 9/2014 | Nanda |
| 2014/0378740 A1 | 12/2014 | Wagner et al. |
| 2015/0105702 A1 | 4/2015 | Wagner et al. |
| 2015/0126913 A1 | 5/2015 | Jurna et al. |
| 2015/0217111 A1* | 8/2015 | Stevenson .............. H01G 4/005 |
| | | 607/63 |
| 2016/0016013 A1 | 1/2016 | Capelli et al. |
| 2016/0067139 A1 | 3/2016 | Katragadda et al. |
| 2016/0166837 A1 | 6/2016 | Strommer et al. |
| 2016/0262778 A1* | 9/2016 | Du ...................... A61B 17/225 |
| 2016/0271419 A1 | 9/2016 | Varghese et al. |
| 2017/0202514 A1* | 7/2017 | Nousiainen .......... A61B 8/4227 |
| 2017/0301474 A1* | 10/2017 | Saito ...................... H01G 4/228 |
| 2018/0078774 A1* | 3/2018 | Strommer ............ A61B 5/0031 |
| 2018/0116905 A1 | 5/2018 | Capelli et al. |
| 2018/0221688 A1 | 8/2018 | Cioanta et al. |

FOREIGN PATENT DOCUMENTS

| | | |
|---|---|---|
| CN | 101146574 | 3/2008 |
| CN | 101155614 | 4/2008 |
| CN | 100530868 | 8/2009 |
| CN | 101610736 | 12/2009 |
| CN | 102057422 | 5/2011 |
| CN | 102247661 | 11/2011 |
| CN | 105209117 | 12/2015 |
| CN | 105246419 | 1/2016 |
| DE | 3150430 | 7/1983 |
| DE | 3710371 | 10/1988 |
| DE | 60008898 | 1/2005 |
| DE | 102007046902 | 4/2009 |
| EP | 0008647 | 3/1980 |
| EP | 0243650 | 11/1987 |
| EP | 0322473 | 7/1989 |
| EP | 0326620 | 8/1989 |
| EP | 2964326 | 1/2016 |
| EP | 3626307 | 3/2020 |
| FR | 2605874 | 5/1988 |
| GB | 2303552 | 2/1997 |
| JP | 53-111689 | 9/1978 |
| JP | S61-293447 | 12/1986 |
| JP | S 61-293447 | 12/1986 |
| JP | 62-192150 | 8/1987 |
| JP | S 63-023775 | 2/1988 |
| JP | S63-183050 | 7/1988 |
| JP | S 63-183050 | 7/1988 |
| JP | 6-7365 | 1/1994 |
| JP | H06-505648 | 6/1994 |
| JP | H 06-505648 | 6/1994 |
| JP | H0673654 | 10/1994 |
| JP | 8-140984 | 6/1996 |
| JP | H 08140984 | 6/1996 |
| JP | 8-194079 | 7/1996 |
| JP | 1996-222472 | 8/1996 |
| JP | H0-8224253 | 9/1996 |
| JP | 9-103434 | 4/1997 |
| JP | H09103434 | 4/1997 |
| JP | H 10192289 | 7/1998 |
| JP | H 10328192 | 12/1998 |
| JP | 2003-500126 | 1/2003 |
| JP | 2004526507 | 9/2004 |
| JP | 2005514142 | 5/2005 |
| JP | 2007-000218 | 1/2007 |

(56) References Cited

FOREIGN PATENT DOCUMENTS

| | | |
|---|---|---|
| JP | 2009-506870 | 2/2009 |
| JP | 2009-518126 | 4/2009 |
| JP | 2009-527262 | 7/2009 |
| JP | 2009-543614 | 12/2009 |
| JP | 2012-516170 | 7/2012 |
| JP | 2013-537559 | 10/2013 |
| JP | 2014-507990 | 4/2014 |
| JP | 2014-525782 | 10/2014 |
| JP | 2016/523602 | 8/2016 |
| JP | 2017-500078 | 1/2017 |
| JP | 61-73644 | 8/2017 |
| KR | 101886863 | 8/2018 |
| RU | 2121812 | 11/1998 |
| RU | 2151559 | 6/2000 |
| TW | 200604017 | 2/2006 |
| TW | I292341 | 1/2008 |
| TW | I350249 | 10/2011 |
| WO | WO 91/10227 | 7/1991 |
| WO | WO-9110227 A1 * | 7/1991 ............ G10K 15/06 |
| WO | WO 2000/071207 | 11/2000 |
| WO | WO 2002/030256 | 4/2002 |
| WO | WO 2004/080147 | 9/2004 |
| WO | WO 2007/067563 | 6/2007 |
| WO | WO 2007/088546 | 8/2007 |
| WO | WO 2007/146988 | 12/2007 |
| WO | WO 2008/052198 | 5/2008 |
| WO | WO 2008/074005 | 6/2008 |
| WO | WO 2008/137942 | 11/2008 |
| WO | WO 2010/086301 | 8/2010 |
| WO | WO 2010/122517 | 10/2010 |
| WO | WO 2011/077466 | 6/2011 |
| WO | WO 2011/091020 | 7/2011 |
| WO | WO 2012/107830 | 8/2012 |
| WO | WO 2013/012724 | 1/2013 |
| WO | WO 2014/138582 | 9/2014 |
| WO | WO 2014/191263 | 12/2014 |
| WO | WO 2015/176001 | 11/2015 |
| WO | WO 2017/165595 | 9/2017 |
| WO | WO 2018/136514 | 7/2018 |

OTHER PUBLICATIONS

Boxman, et al., "Handbook of Vacuum Arc Science and Technology: Fundamentals and Applications," Park Ridge, New Jersey: Noyes Publications, pp. 316-319, 1995.
Chen et al., "The Disappearance of Ultrasound Contiast Bubbles: Observations of Bubble Dissolution and Cavitation Nucleation", *Ultrasound in Med. & Biol.*, 28(6): 793-803, 2002.
Delius, et al. "Biological Effects of Shockwaves: Kidney Haemorrhage by Shock Waves in Dogs—Administration Rate Dependence," *Ultrasound in Medicine & Biology*, 14(8); 689-694, 1988.
Eisenmenger, et al., The First Clinical Results of "Wide-Focus and Low-Pressure ESWL" *Ultrasound in Med. & Biol.*, 28(6), 769-774, 2002.
Eisenmenger, Wolfgang, "The Mechanisms of Stone Fragmentation in ESWL", *Ultrasound in Med. & Biol.*, 27(5), 683-693, 2001.
Gillitzer, et al., "Low-Frequency Extracorporeal Shock Wave Lithotripsy Improves Renal Pelvic Stone Disintegration in a Pig Model," *BJU International*, 176; 1284-1288, 2009.
Ho, et al., "Laser-Tattoo Removal-A Study of the Mechanism and the Optimal Treatment Strategy via Computer Simulations", Lasers in Surgery and Medicine 30:389-391, 2002.
International Preliminary Report on Patentability Issued in Corresponding PCT Application No. PCT/US2017/042122, dated Jan. 22, 2019.
International Search Report and Written Opinion Issued in Corresponding PCT Application No. PCT/US2017/042122, dated Jan. 9, 2018.
International Search Report and Written Opinion Issued in Corresponding PCT Application No. PCT/US 14/21746, dated Sep. 12, 2014.

Kuhn et al., "Impact of Extracorporeal Shock Waves on the Human Skin with Cellulite: A Case Study of an Unique Instance", *Clinical Interventions of Aging*, 3(1):201-210, 2008.
Kuperman-Beade et al., "Laser Removal of Tattoos", *American Journal of Clinical Dermatology*, 2(1):21-25, 2001.
Kuzmin, et al., "Ultrasonic Cavitational Chemical Technologies", *XI Session of the Russian Acoustical Society, Moscow*, Nov. 19-23, 2001.
Madbouly, et al., "Slow Versus Fast Shock Wave Lithotripsy Rate for Urohthiasis: A Prospective Randomized Study," *The Journal of Urology*, 173: 127-130, 2005.
Ng & Liu, "Therapeutic Ultrasound: Its Application in Drug Delivery", *Medicinal Research Reviews*, 22(2), 204-223, 2002.
Ogden et al., "Principles of Shock Wave Therapy," *Clinical Orthopaedics and Related Research*, No. 387, pp. 8-17, 2001.
Ross et al., "Comparison of Responses of Tattoos to Picosecond and Nanosecond Q-Switched Neodymium: YAG Lasers" *ARCH Dermatology*, 134: 167-171, 1995.
Schmitz, et al., "Treatment of Chronic Plantar Fasciopathy with Exliacorporeal Shock Waves (Review)," *Journal of Orthopaedic Surgery and Research*, 8(1); 31, 2013.
Sheth and Pandya, "Melasma: A Comprehensive Update (Part I)", *Journal of the American Academy of Dermatology*, 65:689-697, 2011.
Sheth and Pandya, "Melasma: A Comprehensive Update (Part II)", *Journal of the American Academy of Dermatology*, 65:699-714, 2011.
Solis et al., "Experimental Nonsurgical Tattoo Removal in a Guinea Pig Model with Topical Imiquimod and Tretinoin", *American Society for Dermatologic Surgery*, 28: 83-87, 2002.
Timko & Miller, "In Vitro Quantitative Chemical Analysis of Tattoo Pigments", *ARCH Dermatolology*, 137: 143-147, 2001.
Ushakov, et al., "Impulse Breakdown of Liquids," New York, New York: Springer.
Varma, S., "Tattoo Ink Darkening of a yellow Tattoo after Q-Switched Laser Treatment", *Clinical and Experimental Dermatology*, 27, 461-463, 2002.
Wolfrum et al., "Shock Wave Induced Interaction of Microbubbles and Boundaries", *Physics of Fluids*, 15(10): 2916-2922, 2003.
Extended European Search Report Issued in Corresponding European Patent Application No. 20153807.1, dated Jun. 9, 2020.
Bickle, Abdominal X Rays Made Easy: Calcification, Student BMJ vol. 10, Aug. 2002, 272-274.
Burov, et al., "Nonlinear Ultrasound: Breakdown of Microscopic Biological Structures and Nonthermal Impact on Malignant Tumor," *Doklady Biochemistry and Biophysics*, 383(3), pp. 101-104. (2002).
Falco, "Single-Point Nonlinearity Indicators for the Propagation of High Amplitude Acoustic Signals," Ph.D. Thesis. Graduate Program in Acoustics, The Pennsylvania State University, University Park, PA, May 2007.
Fernando, "A Nonlinear Computational Method for the Propagation of Shock waves in Aero-Engine Inlets Towards A New Model for Buzz-Saw Noise Prediction," 15$^{th}$ AIAA/CEAS Aeroacoustics Conference (30$^{th}$ Aeroacoustics Conference) May 11-13, 2009, 1-18.
International Search Report Issued in Corresponding PCT Patent Application No. PCT/US2018/014053, dated May 4, 2018.
Liu, et al., "Optimized Design of LED Freeform Lens For Uniform Circular Illumination," *Journal of Zhejiang University-Science C*, Computer & Electron, 13(12), 929-936, 2012.
Nana, et al., "Application of the Multiple Low-Energy Q-Switched Laser for the Treatment of Tattoos in 21 Cases," China Aesthetic Medicine, 4(21), 621-622, 2012. (English Abstract).
Partial Supplementary Search Report Issued in Corresponding European Patent Application No. EP18754679.1, dated Jul. 29, 2020.
Reichenberger, "Electromagnetic Acoustic Source for Extracorporeal Generation of Shock Waves in Lithotripsy," Siemens Forsch, 1986, 187-194.
Vogel, et al., "Shock Wave Emission and Cavitation Bubble Generation by Picosecond and Nanosecond Optical Breakdown in Water," J. Acoust. Soc. Am., 100 (1) Jul. 1996.
Office Action Issued in Corresponding Japanese Patent Application No. 2019-012062, dated Jun. 16, 2020.

(56) References Cited

OTHER PUBLICATIONS

Examination Report Issued in Corresponding Taiwan Patent Application No. 106123181, dated Dec. 16, 2020.
International Search Report and Written Opinion issued in Corresponding PCT Application No. PCT/US2020/026425, dated Sep. 2, 2020.
Office Action and Search Report issued in Corresponding Chinese Application No. 201780056472.0, dated Jan. 19, 2022 (English Translation provided).
Office Action issued in Australian Patent Application No. 2021201670, dated Jun. 20, 2022.
Office Action issued in U.S. Appl. No. 16/478,611, dated Jun. 30, 2022.
Troilius, "Effective Treatment of traumatic Tattoos with a Q-switched Nd:YAG laser," Lasers Surg. Med., 22:103-108, 1998.
English translation of Office Action issued in Japanese Patent Application No. 2021-184610, dated Nov. 18, 2022.
Office Action issued in Australian Patent Application No. 2018221251, dated Nov. 10, 2022.
English translation of Office Action issued in Korean Patent Application No. 10-2019-7005043 dated Sep. 28, 2022.
Office Action issued in U.S. Appl. No. 16/087,976 dated Oct. 13, 2022.
Office Communication issued in U.S. Appl. No. 16/904,125, dated Mar. 23, 2023.
Office Communication issued in U.S. Appl. No. 17/096,932, dated Mar. 28, 2023.
Official Action issued in Japanese Patent Application No. 2019-544631, dated Sep. 16, 2022.
Official Action issued in U.S. Appl. No. 13/547,995, dated Sep. 15, 2022.
Official Action issued in U.S. Appl. No. 16/486,920, dated Sep. 14, 2022.
Carlberg, "Upgrading from Stepper to Servo," Yaskawa America Inc., pp. 1-7, 2011.
Manousakas et al., "Development of a system of automatic gap-adjusted electrodes for shock wave generators," Review of Scientific Instruments, 75(11):4811-4819, 2004.
Office Action issued in U.S. Appl. No. 16/478,611, dated Oct. 31, 2022.
Notice of Allowance issued in U.S. Appl. No. 17/648,790, dated Feb. 28, 2023.
Office Communication issued in Japanese Patent Application No. 2018-550349, dated Mar. 7, 2023. (English translation).

* cited by examiner

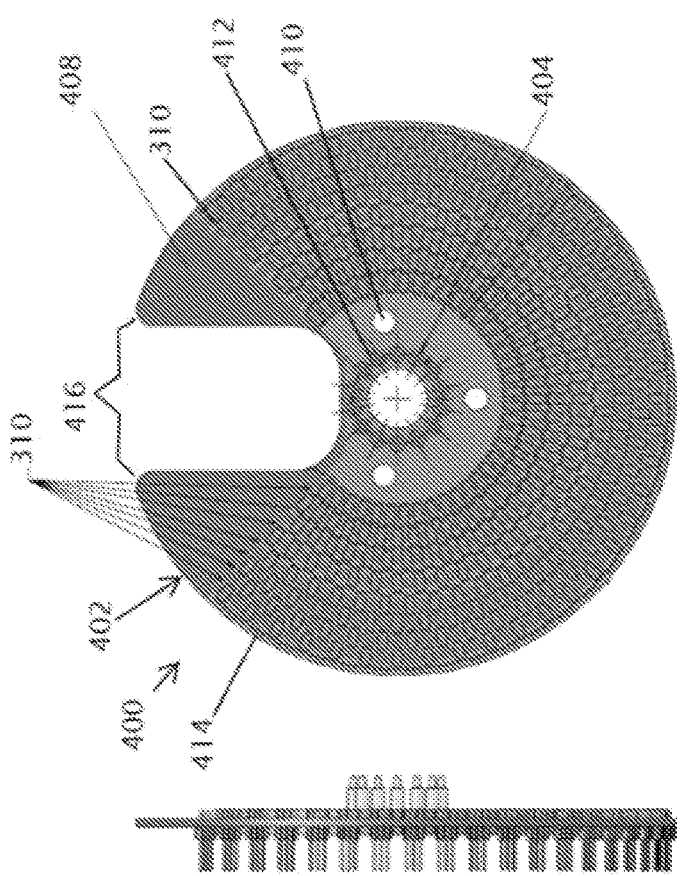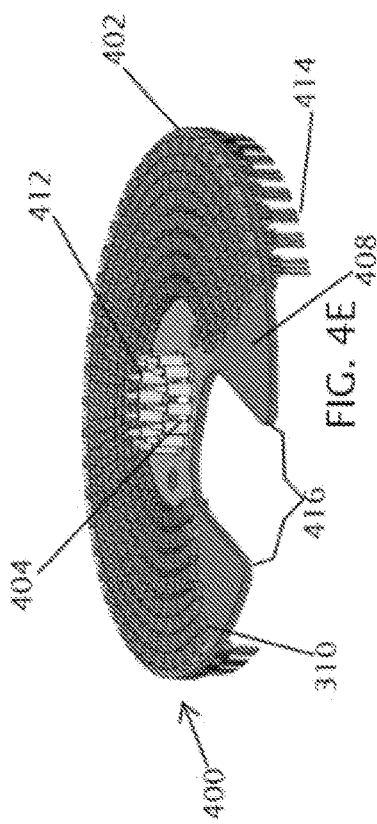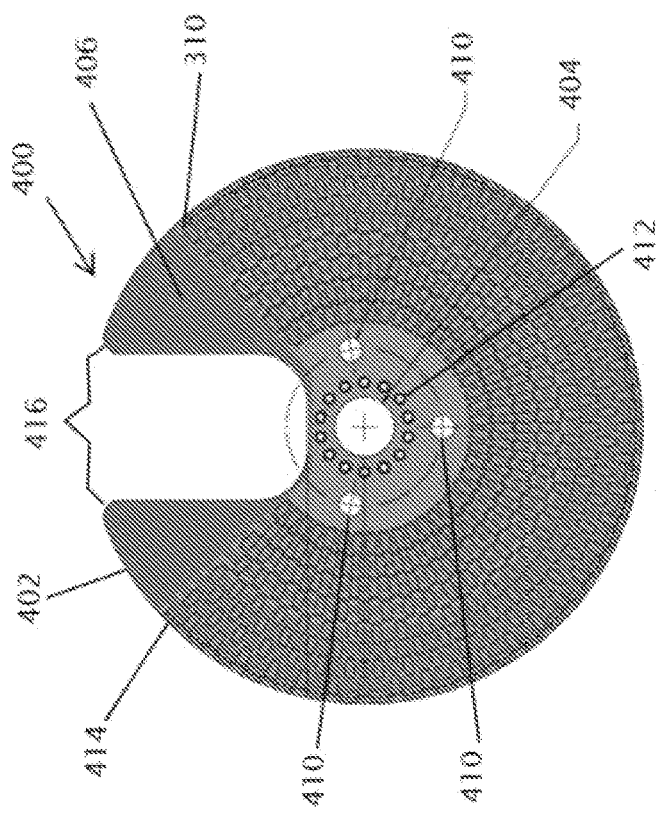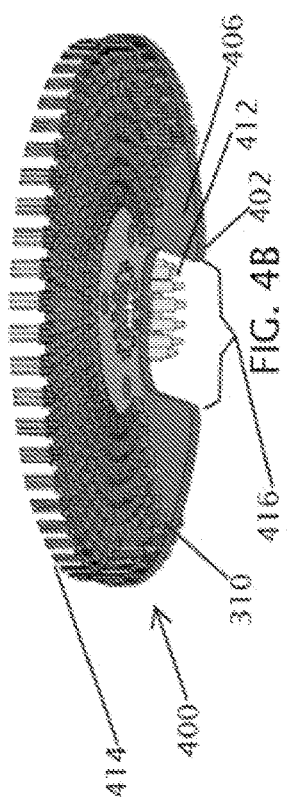

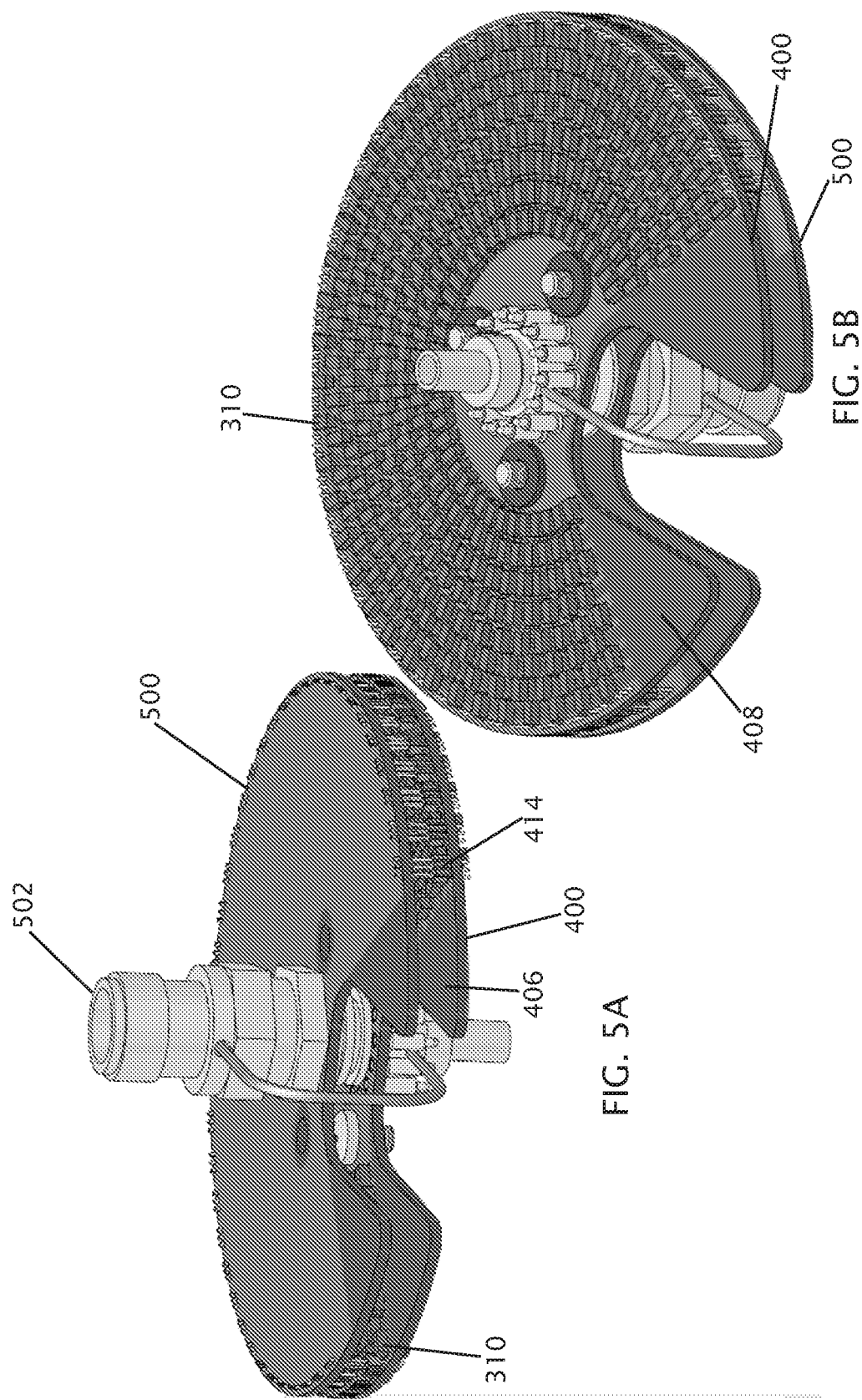

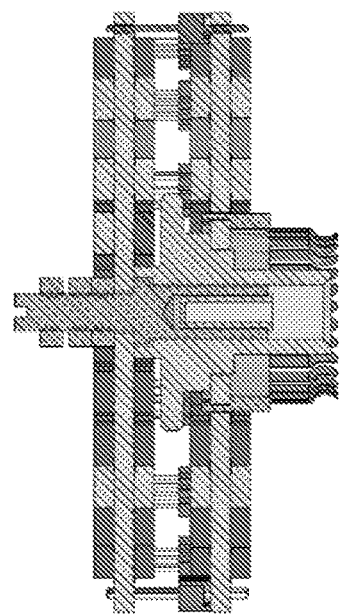
FIG. 6C
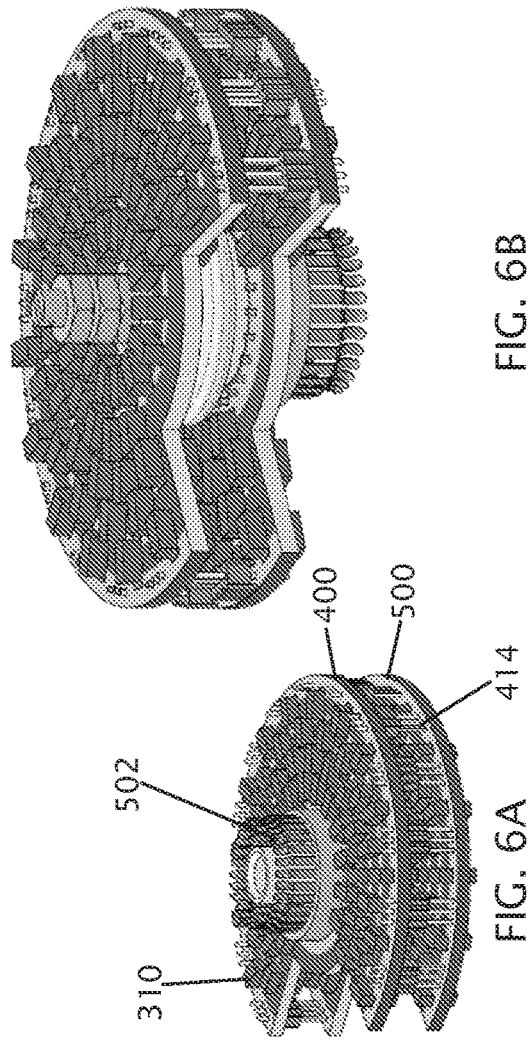
FIG. 6A
FIG. 6B
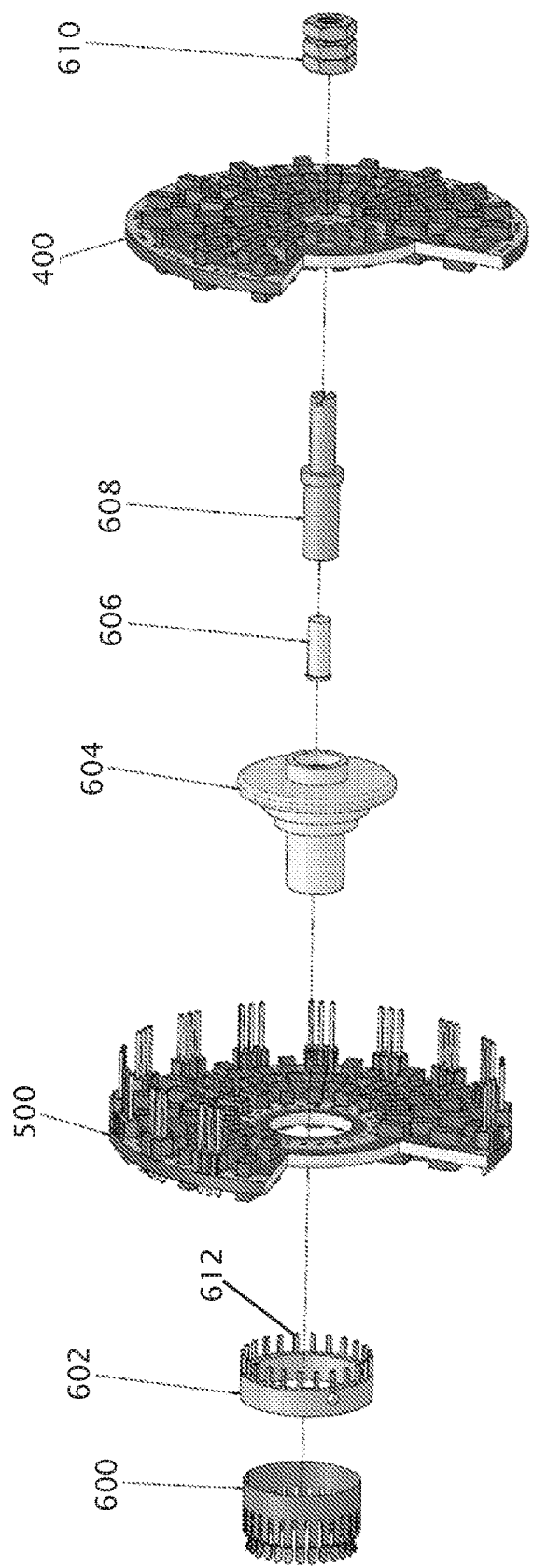
FIG. 6D

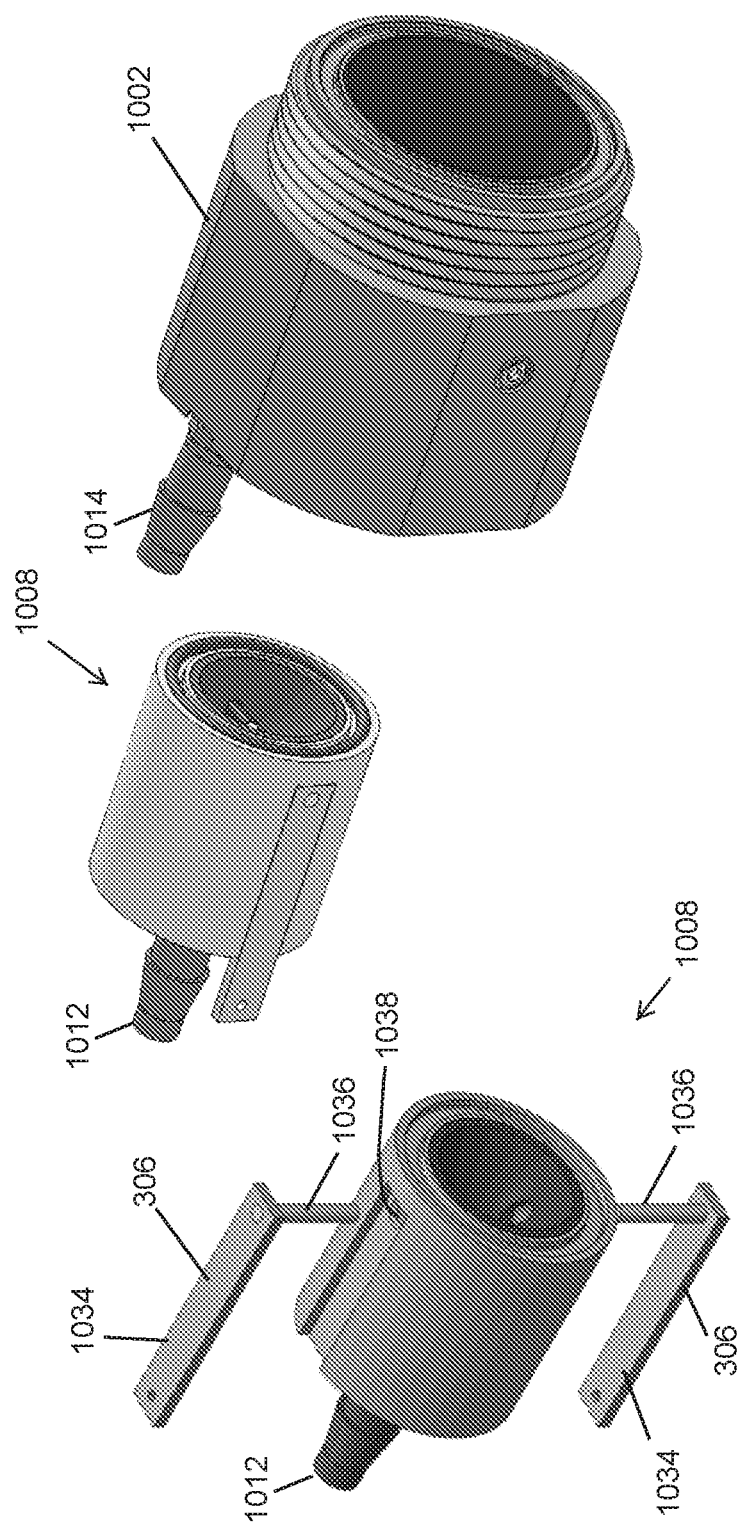

RAPID PULSE ELECTROHYDRAULIC (EH) SHOCKWAVE GENERATOR APPARATUS WITH IMPROVED ELECTRODE LIFETIME

CROSS-REFERENCE TO RELATED APPLICATIONS

This application is a national phase application under 35 U.S.C. § 371 of International Application No. PCT/US2017/042122, filed Jul. 14, 2017, which claims the benefit of U.S. Provisional Application No. 62/365,099 filed Jul. 21, 2016, each of which applications is incorporated into the present application by reference in their respective entireties.

FIELD OF INVENTION

The present invention relates generally to therapeutic uses for shock waves or shockwaves. More particularly, but not by way of limitation, the present invention relates to an apparatus for generating therapeutic shock waves or shockwaves (shock waves with therapeutic uses) with improved electrode lifetime.

DESCRIPTION OF RELATED ART

Acoustic shockwaves have been used for certain therapies for a number of years. "Shock wave" or "shockwave" is generally used to refer to an acoustic phenomenon (e.g., resulting from an explosion or lightning) that creates a sudden and intense change in pressure. These intense pressure changes can produce strong waves of energy that can travel through elastic media such as air, water, human soft tissue, or certain solid substances such as bone, and/or can induce an inelastic response in such elastic media. Methods for creating shock waves for therapeutic uses include: (1) electrohydraulic, or spark gap (EH); (2) electromagnetic, or EMSE; and (3) piezoelectric. Each is based upon its own unique physical principles.

A. Devices and Systems for Shockwave Generation

U.S. patent application Ser. No. 13/574,228 (a national-stage application of PCT/US2011/021692, which published as WO 2011/091020), by one of the present inventors, discloses a device for producing shock waves at a high pulse rate using a transducer. That device includes an acoustic-wave generator configured to emit acoustic waves having at least one frequency between 1 MHz and 1000 MHz; a shockwave housing coupled to the acoustic-wave generator; and a shockwave medium disposed in the shockwave housing; where the apparatus is configured such that if the acoustic-wave generator emits acoustic waves then at least some portion of the acoustic waves will travel through the shockwave medium and form shock waves. That device can be actuated to form shock waves configured to cause particles within a patient to rupture one or more cells of the patient, and the shock waves can be directed to cells of a patient such that the shock waves cause particles to rupture one or more of the cells. This acoustic-transducer device can produce high powered shockwaves at high frequencies or pulse rates.

Additionally, U.S. patent application Ser. No. 13/798,712, also by the present inventors, discloses apparatuses and methods for electrohydraulic generation of shockwaves at a rate of 10 Hz and 5 MHz comprising: a housing defining a chamber and a shockwave outlet; a liquid disposed in the chamber; a plurality of electrodes (e.g., in a spark head or module) configured to be disposed in the chamber to define one or more spark gaps; and a pulse-generation system configured to apply voltage pulses to the electrodes at a rate of between 10 Hz and 5 MHz.

Other systems for producing shockwaves can include an electrohydraulic (EH) wave generator. EH systems can generally deliver similar levels of energy as other methods, but may be configured to deliver that energy over a broader area, and therefore deliver a greater amount of shock wave energy to targeted tissue over a shorter period of time. EH systems generally incorporate an electrode (i.e., a spark plug) to initiate a shock wave. In EH systems, high energy shock waves are generated when electricity is applied to an electrode immersed in treated water contained in an enclosure. When the electrical charge is fired, a small amount of water is vaporized at the tip of the electrode and the rapid, nearly instantaneous, expansion of the vaporized water creates a shock wave that propagates outward through the liquid water. In some embodiments, the water is contained in an ellipsoid enclosure. In these embodiments, the shock wave may ricochet from the sides of the ellipsoid enclosure and converge at a focal point that coincides with the location of the area to be treated.

For example, U.S. Pat. No. 7,189,209 (the '209 Patent) describes a method of treating pathological conditions associated with bone and musculoskeletal environments and soft tissues by applying acoustic shock waves. The '209 Patent describes that shockwaves induce localized trauma and cellular apoptosis therein, including micro-fractures, as well as to induce osteoblastic responses such as cellular recruitment, stimulate formation of molecular bone, cartilage, tendon, fascia, and soft tissue morphogens and growth factors, and to induce vascular neoangiogenesis. The '209 Patent claims several specific implementations of its method. For instance, the '209 Patent claims a method of treating a diabetic foot ulcer or a pressure sore, comprising: locating a site or suspected site of the diabetic foot ulcer or pressure sore in a human patient; generating acoustic shock waves; focusing the acoustic shock waves throughout the located site; and applying more than 500 to about 2500 acoustic shock waves per treatment to the located site to induce micro-injury and increased vascularization thereby inducing or accelerating healing. The '209 Patent discloses a frequency range of approximately 0.5-4 Hz, and application of about 300 to 2500 or about 500 to 8,000 acoustic shock waves per treatment site, which can result in a treatment duration for each treatment site and/or a "total time per treatment" for all sites that is inconveniently large. For example, the '209 Patent discloses total times per treatment for different examples ranging from 20 minutes to 3 hours.

U.S. Pat. No. 5,529,572 (the '572 Patent) includes another example of the use of electro-hydraulically generated shockwaves to produce therapeutic effect on tissues. The '572 Patent describes a method of increasing the density and strength of bone (to treat osteoporosis), comprising subjecting said bone to substantially planar, collimated compressional shock waves having a substantially constant intensity as a function of distance from a shock wave source, and wherein said collimated shock waves are applied to the bone at an intensity of 50-500 atmospheres. The '572 Patent describes the application of unfocussed shock waves to produce dynamic repetitive loading of the bone to increase mean bone density, and thereby strengthen bone against fracture. As described in the '572 Patent, "the unfocussed shock waves preferably are applied over a relatively large surface of the bone to be treated, for example to cover an area of from 10 to 150 $cm^2$. The intensity of the shock waves may be from 50-500 atmospheres. Each shock wave is of duration of a few microseconds, as in a conventional lithotripter, and is preferably applied at a frequency of 1-10 shock waves per second for a period of 5-30 minutes in each treatment. The number of treatments depends on the particular patient."

U.S. patent application Ser. No. 10/415,293 (the '293 Application), which is also published as US 2004/0006288, discloses another embodiment of the use of EH-generated shockwaves to provide a therapeutic effect on tissues. The '293 Application discloses a device, system, and method for the generation of therapeutic acoustic shock waves for at least partially separating a deposit from a vascular structure. The '293 Application describes that the device can produce shockwaves at a pulse rate of about 50 to about 500 pulses per minute (i.e., 0.83 to 8.33 Hz) with a number of pulses per treatment site (in terms of per length of vascular unit being treated) from about 100 to about 5,000 per 1 cm$^2$.

B. Shockwave Rate

Prior art literature has indicated that faster pulse rates using EH systems to provide shockwaves can lead to tissue damage. For example, in one study (Delius, Jordan, & et al, 1988) [2], the effect of shock waves on normal canine kidneys was examined in groups of dogs whose kidneys were exposed to 3000 shockwaves. The groups differed only in the rate of shockwave administration which was 100 Hz and 1 Hz, respectively. Autopsy was performed 24 to 30 hours later. Macroscopically and histologically, significantly more hemorrhages occurred in kidney parenchyma if shockwaves were administered at a rate of 100 Hz (vs 1 Hz). The results showed that kidney damage is dependent on the rate of shockwave administration.

In another study (Madbouly & et al, 2005) [7], slow shockwave lithotripsy rate (SWL) was associated with a significantly higher success rate at a lower number of total shockwaves compared to the fast shockwave lithotripsy rate. In this paper, the authors discussed how human studies have also shown a decrease in the incidence of SWL induced renal injury or need for anesthesia when slower rates of test SWL were used.

In yet another study (Gillitzer & et al, 2009) [5], slowing the delivery rate from 60 to 30 shockwaves per minute also provides a dramatic protective effect on the integrity of real vasculature in a porcine model. These findings support potential strategies of reduced pulse rate frequency to improve safety and efficacy in extracorporeal shockwave lithotripsy.

Soft tissues may transition from elastic to viscous behavior for pulse rates (PRs) between 1 Hz and 10 Hz. As a result, potential damage to tissue from shockwaves at PRs between 1 Hz and 10 Hz is unpredictable when typical lithotripsy power levels are used. Perhaps as a result, the prior art teaches slower PRs and large total times per treatment (TTPT). For example, currently known EH shockwave systems generally deliver PRs of less than 10 Hz and require large total times per treatment (TTPT) (e.g., TTPT periods of minutes or even hours for even a single treatment site). When, as may be typical, a treatment requires repositioning of a device at multiple treatment sites, the TTPT becomes large and potentially impractical for many patients and treatment needs.

While long treatment times may be acceptable for extracorporeal shockwave lithotripsy, the use of shockwaves to provide non-lithotripsy therapeutic effects on tissue in the medical setting is less than optimal if not impractical. For example, the cost of treatment often increases with the time needed to administer a treatment (e.g., due to the labor, facilities and other resource costs allocated to the administration of the treatment). Furthermore, in addition to costs, at some point the duration of providing treatment to the patient becomes unbearable for the patient receiving, and healthcare staff providing, the treatment.

SUMMARY

This disclosure includes embodiments of apparatuses and methods for electrohydraulic generation of rapid acoustic pulses that have improved electrode lifetime. In certain embodiments, this improved electrode lifetime is achieved by utilizing a two stage pulse discharge approach to shock wave generation. According to these embodiments, in the first stage, the pulse-generation system is configured to simultaneously apply voltage pulses to the plurality of electrodes in the electrode chamber such that portions of the liquid contained therein are vaporized to provide an inter-electrode conductive path; and, to apply voltage pulses to a plurality of capacitors located adjacent to said electrodes to charge said plurality of capacitors. In the second stage, the charged plurality of capacitors discharge to the electrodes to generate a short inter-electrode arc, through the established inter-electrode conductive path, resulting in an acoustic shock wave. The short inter-electrode arc minimizes electrode erosion leading to improved electrode lifetime.

The improved lifetime of the electrodes is the result of the fast discharge of the capacitors located adjacent to the electrodes within the chamber. The pulse-generation system is configured to simultaneously apply voltage pulses to the plurality of electrodes in the electrode chamber such that portions of the liquid are vaporized to provide an inter-electrode conductive path; and, to apply voltage pulses to the plurality of capacitors located adjacent to said electrodes to charge said plurality of capacitors. In one embodiment, the plurality of capacitors comprises at least 10 planar capacitors in parallel wherein each capacitor has a capacitance of no greater than 100 nanofarad. In one embodiment, the plurality of planar capacitors is placed on a plurality of stacked circuit boards adjacent to the electrodes and wherein the plurality of planar capacitors is placed on opposing sides of each stackable circuit board in a low-inductance pattern. Locating these capacitors adjacent to the electrodes enables the arc to discharge completely and quickly. Once the capacitors are discharged, the inter-electrode arc ends, which minimizes electrode erosion.

Some embodiments of the present apparatuses (e.g., for generating therapeutic shock waves) comprise: a housing defining a chamber and a shockwave outlet; a liquid disposed in the chamber; a plurality of electrodes configured to be disposed in the chamber to define one or more spark gaps; a plurality of capacitors carried by the housing and in electrical communication with the plurality of electrodes; and a pulse-generation system configured to be coupled to the plurality of electrodes such that: (i) the housing is movable relative to the pulse-generation system, and (ii) the pulse-generation system is in electrical communication with the plurality of electrodes and the plurality of capacitors; where the pulse-generation system is configured to apply voltage pulses simultaneously to: the plurality of electrodes (e.g., to begin to vaporize and ionize portions of the liquid to provide at least one inter-electrode conductive path between the plurality of electrodes, and the plurality of capacitors to charge the plurality of capacitors); and where the plurality of capacitors are configured to, upon reaching a threshold charge, discharge to the plurality of electrodes to generate one or more arcs along the one or more inter-electrode conductive paths to vaporize additional portions of the liquid and generate one or more acoustic shock waves.

In some embodiments of the present apparatuses, the pulse-generation system is configured to provide an inter-electrode conductive path by applying voltage to charge the plurality of capacitors during the period that the pulse generation system applies voltage to the plurality of electrodes.

Some embodiments of the present apparatuses (e.g., for generating therapeutic shock waves) comprise: a housing defining a chamber and a shockwave outlet, the chamber being configured to be filled with a liquid; a plurality of electrodes configured to be disposed in the chamber to define one or more spark gaps; a plurality of capacitors carried by the housing and in electrical communication with the plurality of electrodes; and a pulse-generation system configured to be coupled to the plurality of electrodes such that: (i) the housing is movable relative to the pulse-generation system, and (ii) the pulse-generation system is in electrical communication with the plurality of electrodes and the plurality of capacitors; where the pulse-generation system is configured to apply voltage pulses simultaneously to: the plurality of electrodes (e.g., to begin to vaporize and ionize portions of the liquid to provide at least one inter-electrode conductive path between the plurality of electrodes), and the plurality of capacitors to charge the plurality of capacitors; where the plurality of capacitors are configured to, upon reaching a threshold charge, discharge to the plurality of electrodes to generate one or more arcs along the one or more inter-electrode conductive paths to vaporize additional portions of the liquid and generate one or more acoustic shock waves.

Some embodiments of the present apparatuses (e.g., for generating therapeutic shock waves) comprise: a housing defining a chamber and a shockwave outlet, the chamber being configured to be filled with a liquid; a plurality of electrodes configured to be disposed in the chamber to define one or more spark gaps; a plurality of capacitors carried by the housing and in electrical communication with the plurality of electrodes; and where the plurality of electrodes is configured to be coupled to a pulse-generation system such that: (i) the housing is movable relative to the pulse-generation system, and (ii) the pulse-generation system is in electrical communication with the plurality of electrodes and the plurality of capacitors such that the plurality of electrodes and the plurality of capacitors can simultaneously receive voltage pulses from the pulse-generation system; and where the plurality of capacitors are configured to, upon reaching a threshold charge, discharge to the plurality of electrodes.

In some embodiments of the present apparatuses, each of the plurality of capacitors is planar. In some embodiments, the plurality of capacitors are arranged in a circuit having an overall inductance of between 2 nH and 200 nH. In some embodiments, the plurality of capacitors comprises between 2 and 20 sets of capacitors with the sets of capacitors connected in parallel. In some embodiments, each set of capacitors comprises fewer than 50 capacitors. In some embodiments, each set of capacitors comprises 10 or more capacitors in series.

In some embodiments of the present apparatuses, each capacitor has a capacitance of no greater than 100 nanofarad.

In some embodiments of the present apparatuses, the plurality of capacitors is coupled to a plurality of stackable circuit boards. In some embodiments, the plurality of capacitors are arranged in a plurality of circular patterns. In some embodiments, the plurality of stackable circuit boards comprises a first stackable circuit board, and a second stackable circuit board coupled to the first stackable circuit board. In some embodiments, a first portion of the plurality of capacitors is coupled to the first stackable circuit board, and a second portion of the plurality of capacitors is coupled to the second stackable circuit board. In some embodiments, the first portion of the plurality of capacitors is disposed on a first side of a first stackable circuit board, and the second portion of the plurality of capacitors is disposed on a second side of a second stackable circuit board, and the second side of the second circuit board is opposite the first side of the first stackable circuit board. In some embodiments, the first stackable circuit board and the second stackable circuit board are circular. In some embodiments, a first portion of the plurality of capacitors is coupled to the first stackable circuit board and a second portion of the plurality of capacitors is coupled to the second stackable circuit board. In some embodiments, the first portion of the plurality of capacitors is coupled to the first stackable circuit board in a circular pattern; and the second portion of the plurality of capacitors is coupled to the second stackable circuit board in a circular pattern. In some embodiments, each set of capacitors comprises 10 or more capacitors in series. In some embodiments, the first stackable circuit board further comprises an outer edge and a center, the second stackable circuit board further comprises an outer edge and a center; and the first portion of the plurality of capacitors is configured to cause current to flow from the outer edge of the first stackable circuit board towards the center of the first stackable circuit board, and the second portion of the plurality of capacitors is configured to cause current to flow from the outer edge of the second stackable circuit board towards the center of the second stackable circuit board. In some embodiments, the first stackable circuit board is electrically coupled to the second stackable circuit board by connectors disposed along the outer edges of the stackable circuit boards. In some embodiments, the plurality of stackable circuit boards each have a thickness of between 0.02 inches and 0.2 inches.

In some embodiments of the present apparatuses, the plurality of capacitors each have length of between 2 mm and 4 mm, and a width of between 1 mm and 3 mm.

In some embodiments of the present apparatuses, the plurality of capacitors comprises at least 100 capacitors.

Some embodiments of the present capacitor-array apparatus (e.g., for use in generating therapeutic shock waves) comprise: one or more circuit boards; and a plurality of capacitors coupled to the one or more circuit boards; where a first portion of the capacitors is arranged in a first pattern defined by a plurality of capacitor sets, a second portion of the plurality of capacitors is arranged in a second pattern defined by a plurality of capacitor sets, each capacitor set comprises two or more of the capacitors connected in series; the capacitor sets defining the first pattern are connected in parallel, and the capacitor sets defining the second pattern are connected in parallel; and where the one or more circuit boards are configured to be coupled to an electrode such that the electrode is in electrical communication with the capacitors and is fixed in at least two degrees of freedom relative to the one or more circuit boards.

In some embodiments of the present capacitor-array apparatuses, the plurality of capacitors are planar. In some embodiments, the plurality of capacitors are arranged in a circuit having an overall inductance of between 2 nH and 200 nH. In some embodiments, the plurality of capacitors comprises between 2 and 20 sets of capacitors with the sets of capacitors connected in parallel. In some embodiments, each set of capacitors comprises fewer than 50 capacitors.

In some embodiments of the present capacitor-array apparatuses, each set of capacitors comprises 10 or more capacitors in series.

In some embodiments of the present capacitor-array apparatuses, each capacitor has a capacitance of no greater than 100 nanofarads.

In some embodiments of the present capacitor-array apparatuses, the one or more circuit boards comprises a plurality of stackable circuit boards. In some embodiments, the first and second patterns are circular. In some embodiments, the plurality of stackable circuit boards comprises a first stackable circuit board, and a second stackable circuit board coupled to the first stackable circuit board. In some embodiments, the first portion of the capacitors is coupled to the first stackable circuit board, and the second portion of the capacitors is coupled to the second stackable circuit board. In some embodiments, the first portion of the capacitors is disposed on a first side of a first stackable circuit board, and the second portion of the plurality of capacitors is disposed on a second side of a second stackable circuit board, and the second side of the second circuit board is opposite the first side of the first stackable circuit board. In some embodiments of the present capacitor-array apparatuses, the first portion of the plurality of capacitors is coupled to the first stackable circuit board in a circular pattern; and the second portion of the plurality of capacitors is coupled to the second stackable circuit board in a circular pattern. In some embodiments, each set of capacitors further comprises 10 or more capacitors connected in parallel. In some embodiments, the first stackable circuit board further comprises an outer edge and a center, the second stackable circuit board further comprises an outer edge and a center; and the first portion of the plurality of capacitors is configured to cause current to flow from the outer edge of the first stackable circuit board towards the center of the first stackable circuit board, and the second portion of the plurality of capacitors is configured to cause current to flow from the outer edge of the second stackable circuit board towards the center of the second stackable circuit board. In some embodiments, the first stackable circuit board is electrically coupled to the second stackable circuit board by connectors disposed along the outer edges of the stackable circuit boards. In some embodiments, the plurality of stackable circuit boards each have a thickness of between 0.02 inches and 0.2 inches.

In some embodiments of the present capacitor-array apparatuses, the plurality of capacitors each have length of between 2 mm and 4 mm, and a width of between 1 mm and 3 mm.

In some embodiments of the present capacitor-array apparatuses, the plurality of capacitors comprises at least 100 capacitors.

Some embodiments of the present methods (e.g., of producing a compressed acoustic wave using an apparatus for generating therapeutic shock waves), comprising: applying voltage pulses to a plurality of electrodes in a chamber defined by a housing and filled with liquid such that portions of the liquid begin to vaporize and ionize to provide an inter-electrode conductive path; applying voltage to a plurality of capacitors carried by the housing and in electrical communication with the plurality of electrodes to charge the plurality of capacitors; and upon the plurality of capacitors reaching a threshold charge, discharging the plurality of capacitors to the electrodes to generate an inter-electrode arc along the established inter-electrode conductive path and thereby generate of at least one acoustic shock wave. In some embodiments, the voltage pulses applied to the plurality of electrodes is between 500 V and 10,000 volts (V). In some embodiments, the voltage pulses applied to the plurality of capacitors is between 500 V and 10,000 V.

The term "coupled" is defined as connected, although not necessarily directly, and not necessarily mechanically; two items that are "coupled" may be unitary with each other. The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the terms "substantially," "approximately," and "about" may be substituted with "within [a percentage] of" what is specified, where the percentage includes 0.1, 1, 5, and 10 percent. In the disclosed embodiment, the term "adjacent" is generally defined located in the same discrete chamber, housing, or module.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a system or apparatus that "comprises," "has," "includes" or "contains" one or more elements possesses those one or more elements, but is not limited to possessing only those elements. Likewise, a method that "comprises," "has," "includes" or "contains" one or more steps possesses those one or more steps, but is not limited to possessing only those one or more steps.

Further, a structure (e.g., a component of an apparatus) that is configured in a certain way is configured in at least that way, but it can also be configured in other ways than those specifically described.

Any embodiment of any of the present systems, apparatuses, and methods can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

Details associated with the embodiments described above and others are presented below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers. The figures are drawn to scale (unless otherwise noted), meaning the sizes of the depicted elements are accurate relative to each other for at least the embodiment depicted in the figures.

FIG. 4A-4E depict various views of one embodiment of a stackable circuit board comprising a plurality of capacitors.

FIGS. 5A-5E depict various views of a second embodiment of a capacitor array affixed to a pair of coupled stackable circuit boards.

FIGS. 6A-6D depict various views of a capacitor array affixed to a pair of coupled stackable circuit boards and coupling components.

FIGS. 11A and 11B depict parts of the assembly of the probe of FIG. 10.

DESCRIPTION OF ILLUSTRATIVE EMBODIMENTS

Certain embodiments of the present systems and apparatuses are configured to generate high-frequency shock waves while having an improved electrode lifetime. In some embodiments, the generated EH shock waves can be used in medical and/or aesthetic therapeutic applications (e.g., when directed at and/or delivered to target tissue of a patient). Examples of medical and/or aesthetic therapeutic applications in which the present systems can be used are disclosed in: (1) U.S. patent application Ser. No. 13/574,228, published as US 2013/0046207; (2) U.S. patent application Ser. No. 13/547,995, published as, published as US 2013/0018287; and (3) U.S. patent application Ser. No. 13/798,710, published as US 2014/0257144, each of which are incorporated here in their entireties.

In one embodiment, the apparatus for electrohydraulic generation of shockwaves comprises: a housing defining a chamber and a shockwave outlet; a liquid disposed in the chamber; a plurality of electrodes (e.g., in the spark head or module) configured to be disposed in the chamber to define one or more spark gaps; and a pulse generation system configured to apply voltage pulses to the electrodes at a rate of between 10 Hz and 5 MHz. The rate of voltage pulses may be at rates of 25 Hz, 50 Hz, 75 Hz, 100 Hz, 150 Hz, 200 Hz, 250 Hz, 300 Hz, 400 Hz, 500 Hz, 600 Hz, 700 Hz, 800 Hz, 900 Hz, 1 KHz, 5 KHz, 10 KHz, 25 KHz, 50 KHz, 100 KHz, 200 KHz, 300 KHz, 400 KHz, 500 KHz, 600 KHz, 700 KHz, 800 KHz, 900 KHz, 1 MHz, 2 MHz, 3 MHz, and 4 MHz.

A. Prior Art Systems

Figure 1:
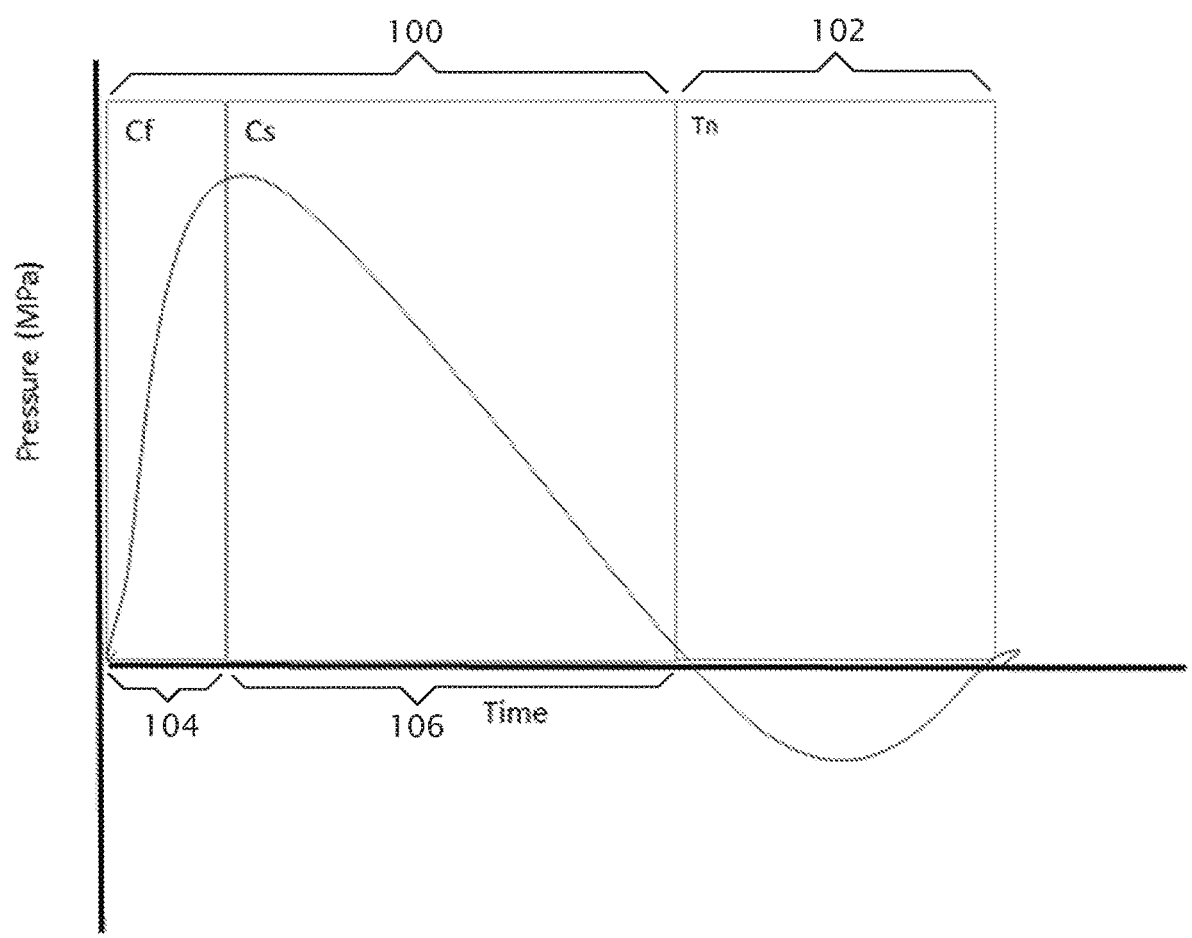
FIG. 1 is a graph illustrating an acoustic wave from prior art electrohydraulic systems.

Referring now to the drawings, FIG. 1 depicts a typical pulse discharge from prior art electrohydraulic systems which produce a broad frequency spectrum acoustic wave (typically in the range of 16 Hz to 30 MHz) consisting of a large compressive pulse wave 100, followed by a small tensile wave 102. The compressive pulse wave 100 consists of two parts: a fast rise acoustic front 104 (also referred to as a shock wave front) followed by a long compressive acoustic tail 106. The fast acoustic front 104 occurs on a time scale of nanoseconds whereas the long compressive acoustic tail 106 occurs on a time scale of microseconds.

Such prior art electrohydraulic systems create a pulse discharge event between two electrodes that takes place in four stages: (1) inter-electrode saline heating and initial vaporization; (2) vapor ionization; (3) inter-electrode arc formation; and (4) intense arc.

Figure 2A:
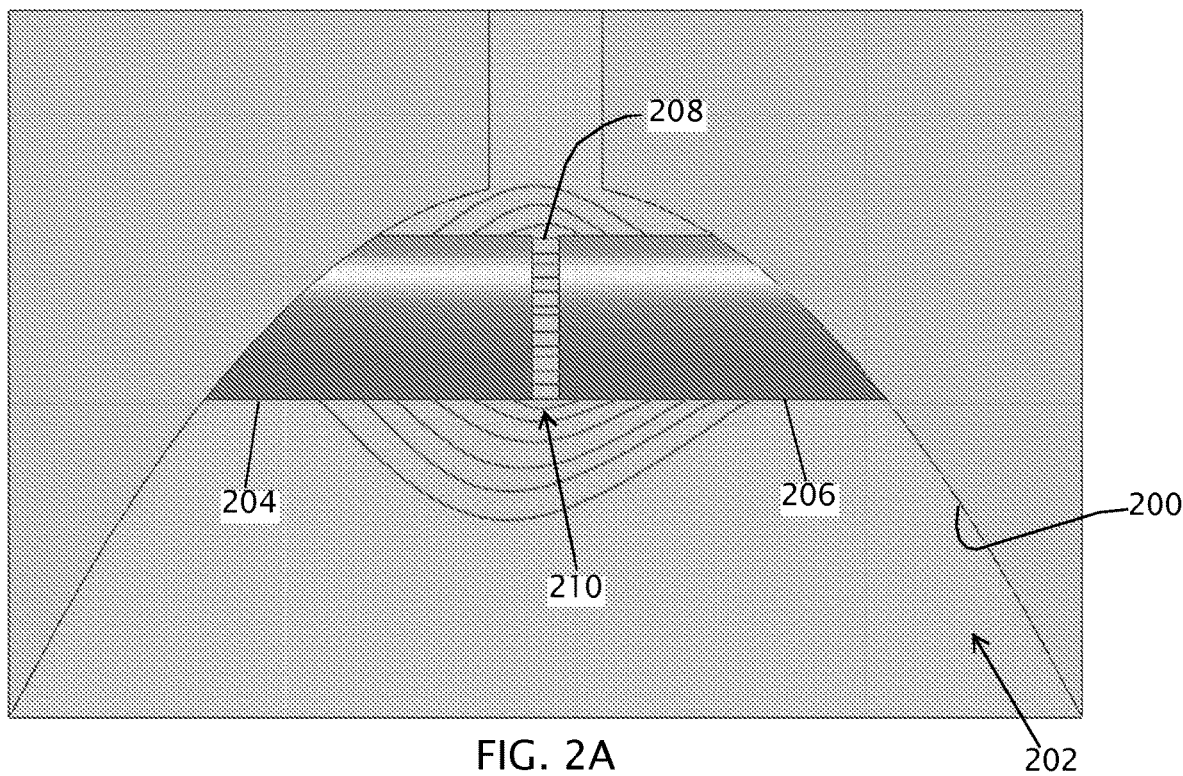
FIG. 2A depicts stage 1 of a pulse generation system: inter-electrode saline heating and initial vaporization.

FIG. 2A depicts Stage 1 of the prior art pulse discharge event: inter-electrode saline heating and initial vaporization. During this stage of the pulse, a chamber 200 is filled with saline 202. Next, a pulse-generation system applies voltage directly to the electrodes 204, 206 to produce an inter-electrode conductive path 208. Specifically, current 210 is conducted through the bulk amount of saline 202 from one electrode 204 to another 206. This results in the saline 202 being heated resulting in portions of the saline 202 being vaporized at initial bubble nucleation sites located on the surface tips of the electrodes 204, 206. Because the electrical conductivity of saline increases with temperature, during this stage the electrode current rises as the temperature of the saline increases. At this stage there is no electrode damage during the saline heating and initial vaporization. The current is approximately evenly distributed across the surface tips of the electrodes 204, 206 and the temperature of the saline is low (up to approximately 100° C.) while overall impedance is high (approximately 50Ω for 1% saline).

Figure 2B:
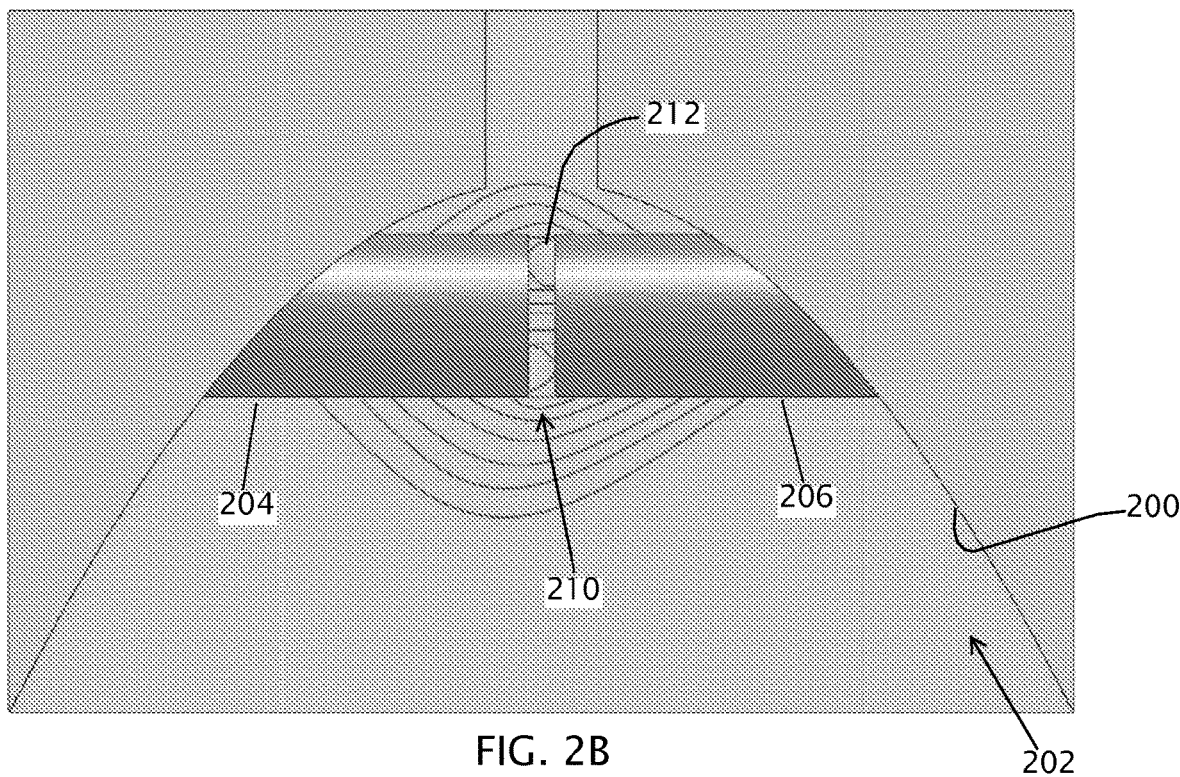
FIG. 2B depicts stage 2 of a pulse generation system: inter-electrode vapor ionization.

FIG. 2B depicts Stage 2 of the prior art pulse discharge event: inter-electrode vapor ionization, which overlaps with Stage 1 as depicted in FIG. 2A. During this stage of the pulse, current 210 is still being primarily conducted through the bulk amount of saline 202 from one electrode 204 to another 206. Saline 202 continues to vaporize and expand from the initial bubble nucleation sites. Once the saline 202 vaporizes and its density is low enough, the increased free paths of the electrons allow them to acquire the energy sufficient for collisional ionization, and avalanche plasma discharges 212 are formed. As with Stage 1, negligible damage to the electrode occurs during this stage. Ion bombardment can cause electrode material removal through sputtering, but rates are extremely low when compared to Stages 3 and 4 of the pulse discharge event. Overall impedance is high (approximately 50Ω for 1% saline).

Figure 2C:
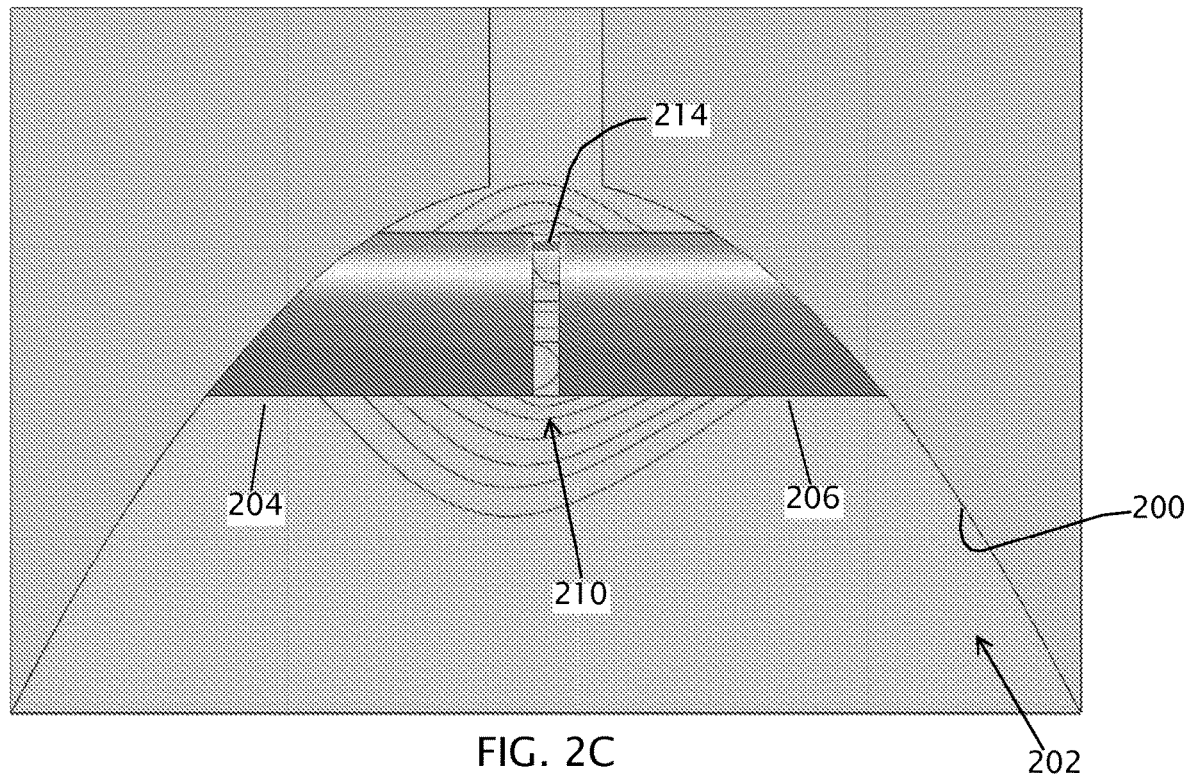
FIG. 2C depicts stage 3 of a pulse generation system: inter-electrode arc formation.

FIG. 2C depicts Stage 3 of the prior art pulse discharge event: inter-electrode arc formation. During this stage of the pulse, multiple events happen almost simultaneously. The discharge through the saline vapor plasma layer causes cathode and anode spots to form on the surfaces of the electrodes. These tiny, intense jets of electrode material and electrons supply the conductive material necessary to form a full arc 214. The jets emanating from the cathode and anode spots begin to connect and transition to the intense arc of Stage 4. The net current across the electrodes 204, 206 begins to spike as the initial arc 214 causes rapid and complete saline vaporization and arc spread. Overall impedance begins to drop from approximately 50Ω to 0.1Ω.

Figure 2D:
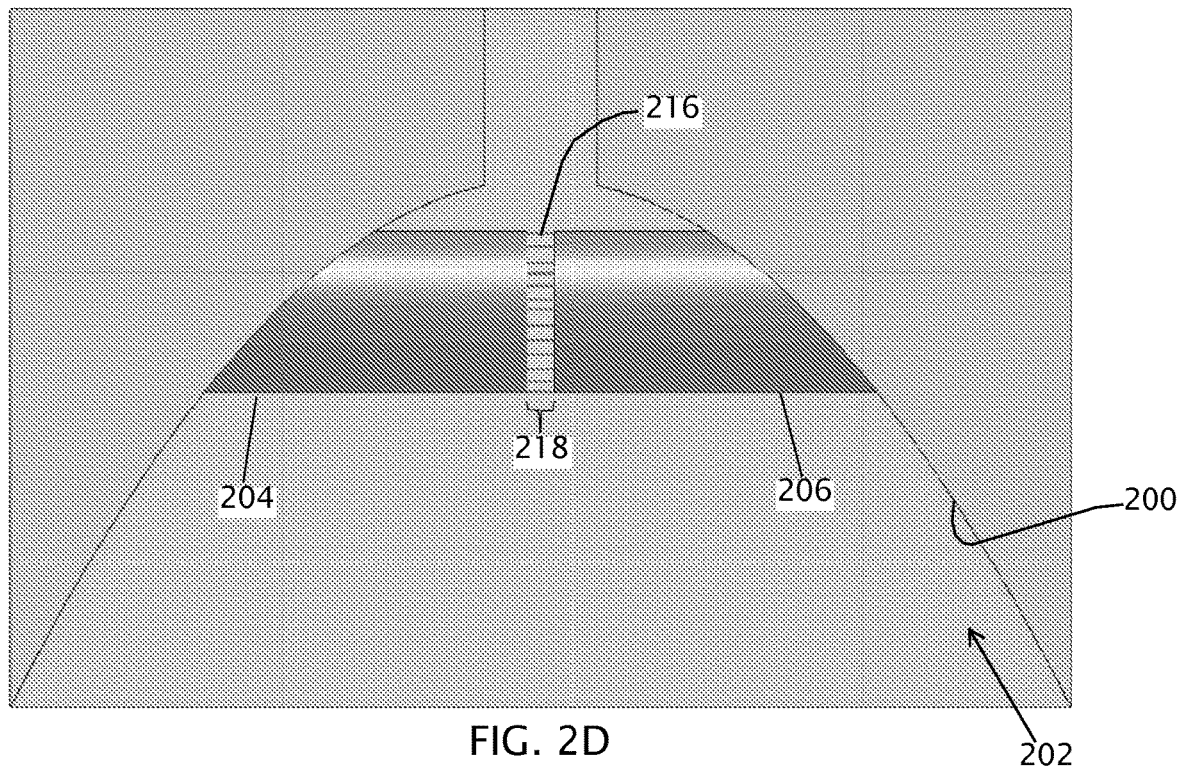
FIG. 2D depicts stage 4 of a pulse generation system: inter-electrode intense arc.

FIG. 2D depicts Stage 4 of the prior art pulse discharge event: inter-electrode intense arc., The intense arc mode 216 is very bright and appears to cover the anode and cathode, and fill the electrode gap 218. Another and cathode spots are present and are continuously ejecting electrode material into the gap 218 which supplies the feeder material for the low-impedance arc. The intense arc mode 216 produced by prior art pulse-generation systems is characterized by sever erosion at the anode and cathode [1]. The arc voltage is low and the current is high, due to the low overall impedance (approximately 0.1Ω). Anode erosion is typically more severe than cathode erosion because the anode spots tend to be fewer and more intense, while the cathode spots are mot numerous and distributed [1].

The severe erosion of the electrodes 204, 206 using prior art electrohydraulic systems limits the lifetime of the electrodes in those systems. Because many applications for electrohydraulic systems require large numbers or fast rates of pulses to be effective, the prior art approaches for generating these acoustic waves result in a lowering the limited lifetime of the electrodes 204, 206 requiring either frequent electrode replacement or the use of an expensive, complicated electrode feeder system. Due to the limited electrode lifetime, these requirements have constrained electrohydraulic systems' commercial usefulness.

B. Improved Systems, Components, and Methods

Certain embodiments of the present apparatuses and methods are configured to electrohydraulically generate shockwaves while providing improved electrode lifetime. Certain embodiments achieve improved electrode lifetime by utilizing a two stage pulse discharge approach to shockwave generation. In some embodiments, in the first stage, the pulse-generation system is configured to simultaneously: (1) apply voltage pulses to a plurality of electrodes in an electrode chamber such that a portion of a liquid contained within the chamber are vaporized to provide an inter-electrode conductive path; and (2) apply voltage pulses to charge a plurality of capacitors located adjacent to the plurality of electrodes. In such embodiments, in the second stage, the charged plurality of capacitors discharge to generate short inter-electrode arc through the established inter-electrode conductive path resulting in an acoustic shockwave. A shorter inter-electrode arc can minimize electrode erosion, and thereby lead to improved electrode lifetime.

In electrohydraulic shockwave generation, high capacitance may be required to obtain the required peak pulse current with the desired waveform at the electrodes. In some of the present embodiments, large capacitors may be disposed close to the electrodes may be able to provide the high voltage pulse to the electrodes necessary to produce a short inter-electrode arc. However, the use of repeated large voltage and current phase discharges required to generate pulse shockwaves may cause damage to large capacitors, which may in turn lead to shockwave generator failure. The capacitor damage sustained in these prior art systems is theorized to be secondary to the piezoelectric effect of the capacitor plates leading to mechanical failure. This problem can limit the ability to produce a commercially viable rapid pulse shockwave generator that has an electrode lifetime of acceptable length.

In some of the present embodiments, a plurality of small capacitors in parallel, arranged (e.g., in a low-inductance pattern) adjacent to the electrodes (e.g., in or on a hand-held housing in which the electrodes are disposed) can be used to produce a short inter-electrode arc. In this embodiment, a plurality of small capacitors in parallel, arranged in a low-inductance pattern adjacent to electrodes is able to provide the repeated and rapid large voltage and current pulse discharges required to generate rapid pulse shockwaves without damage to the capacitors. The piezoelectric effect on the materials for each small capacitor is limited when used within the plurality of small capacitors in parallel to generate rapid pulse shockwaves. As a result, in such embodiments, catastrophic capacitor mechanical failure is avoided, thereby improving the commercially viability of rapid pulse shockwave generators.

In some of the present embodiments, a plurality of small capacitors in parallel may be placed in a plurality of stacked circuit boards so as to condense the area required for the capacitors. Additionally, placing the plurality of small capacitors on opposing sides of each stackable circuit board results not only in further reduction of surface area required for the capacitors, but also a reduction of the inductance caused by the use of the plurality of capacitors.

Figure 3:
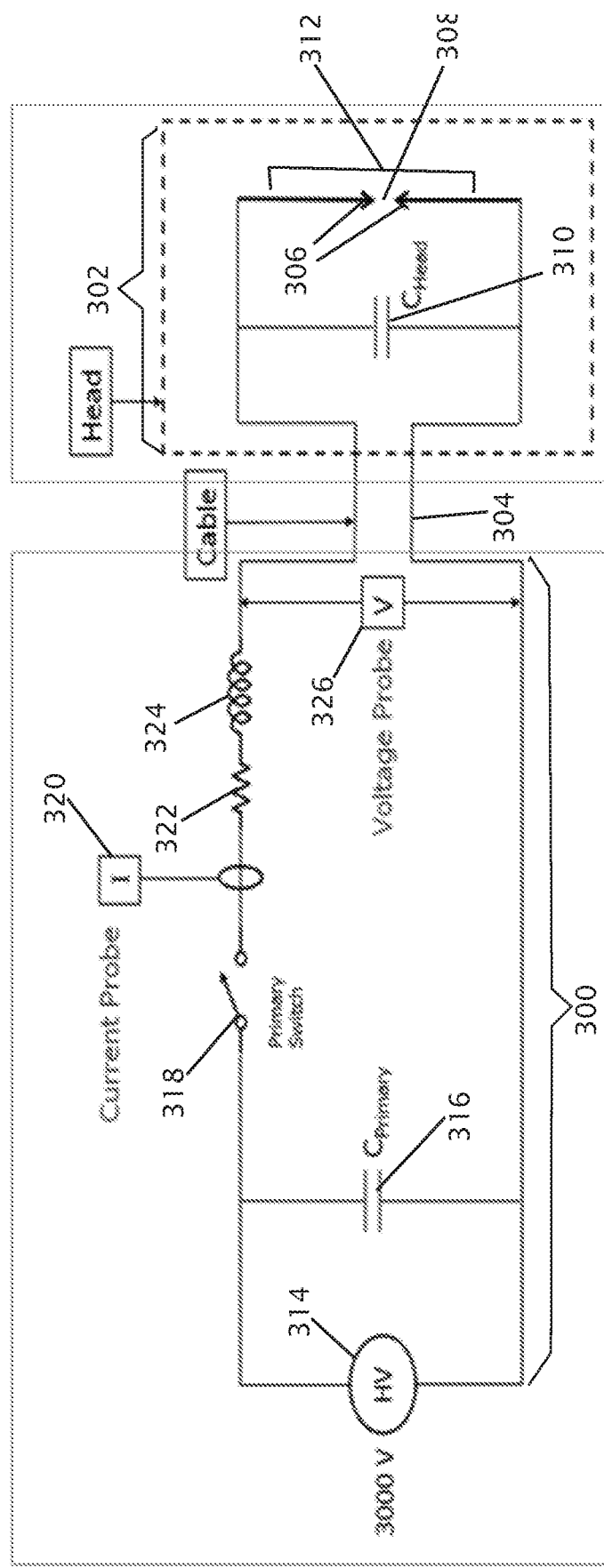
FIG. 3 depicts a schematic diagram of one embodiment of an electrohydraulic shock wave generation system for use in or with some embodiments of the present systems.

FIG. 3 depicts a representative schematic of one embodiment of the disclosed electrohydraulic apparatus. In the embodiment shown, a pulse-generation system 300 is coupled to a head 302 by a cable 304. The head 302 includes a plurality of electrodes 306 configured to define one or more spark gap 308, and a plurality of capacitors 310 (e.g., with the electrodes and capacitors carried by a housing). As described below, the capacitors may, for example, be configured in a low-inductance pattern. In some such embodiments, the housing or body of the head 302 defines a housing within which the plurality of electrodes 306 is disposed (e.g., with a portion of each electrode extending into the chamber), and the plurality of capacitors 310 is carried by the housing (and/or may be disposed in a chamber 312). The chamber 312 is configured to be filled with a liquid. In the embodiment shown, pulse-generation system 300 comprises a high voltage power supply 314, a capacitor 316, a primary switch 318, a current probe 320, a resistor 322, an inductor 324, and a voltage probe 326. The high voltage power supply 314 may for example, be configured to supply 3000 volts (V). The pulse-generation system 300 is configured to apply voltage pulses to the plurality of electrodes 306 such that portion of the liquid disposed in the chamber 312 are vaporized to provide an inter-electrode conductive path. The pulse-generation system 300 is also configured to (e.g., simultaneously) apply voltage to the plurality of capacitors 310 within the chamber. Once charged, the plurality of capacitors 310 can discharge within the established inter-electrode conductive path to produce a short inter-electrode discharge arc. This discharge arc then results in the formation of a shockwave.

In some embodiments, such as the one shown in FIGS. 4A-4E, at least a portion of the plurality of capacitors 310 is coupled to a stackable circuit board 400 in a circular, low inductance pattern on both the top side 408 and the bottom side 406 of the stackable circuit board 400. FIG. 4A depicts a bottom-up view of one embodiment of a stackable circuit board 400 having a plurality of capacitors 310 coupled to the bottom side 406 of the stackable circuit board 400. In the embodiment shown, the stackable circuit board 400 is circular, having an outer edge 402 and an center aperture 404. Surrounding the center aperture 404, the stackable circuit board 400 has a plurality of additional apertures 410 and a plurality of pins 412. In this embodiment, fourteen (14) pins 412 are coupled to the stackable circuit board 400. Other embodiments may include 5, 6, 7, 8, 9, 10, 11, 12, 13, 15, 16, 17, 18, 19, 20 or more pins 412 surrounding the center aperture 404. Pins 412 may, for example, be pogo pins or other connectors configured to establish, at least temporarily, an electrical connection between multiple circuit boards. Additionally, in the embodiment shown, the stackable circuit board 400 has a plurality of board-to-board connectors 414 running around its outer edge 402. Connectors 414 may be arranged in single row as shown, or in two rows, and facilitate electrically coupling the stackable circuit board 400 with additional circuit boards. Connectors 414 may, for example, be configured to operate across a range of temperatures between −55° C. and 125° C.

In the embodiment shown, capacitors 310 are coupled to stackable circuit boards 400 in a low inductance pattern. As shown, a low inductance pattern of capacitors may comprise a plurality of sets of capacitors, each set of capacitor comprising of a plurality of individual capacitors. In the low inductance pattern, the sets of capacitors are arranged such that each set is in parallel with each other set. According to one embodiment, as shown in FIGS. 4A-4E, each set of capacitors is coupled to the stackable circuit board 400 such that one capacitor is coupled to the board 400 near the center aperture 404 and a plurality of additional capacitors are coupled to the board 400 such that they are in electrical communication with one another and extend radially away from the center aperture 404 towards the outer edge 402. This portion of capacitors from the set is further configured such that they are in electrical communication with an additional portion of capacitors situated on the opposing side of the board (or another board, as shown in FIGS. 6A-6D). This additional portion of capacitors is similarly configured such that they extend in series from the edge of the board 402 towards the center aperture 404. According to the embodiment described, the overall configuration of capacitors is such that multiple sets of capacitors, each with a portion of the overall plurality of capacitors, extend from the center aperture 404 outward to the center edge 402, continue to the opposite side of the board (or to another board), then extend from the edge of the board 402 back towards the center aperture 404. Capacitors 310, when so configured, may cause current to flow from the outer edge 402 of the stackable circuit board 400 towards the center aperture 404 or from the center aperture 404 of the stackable circuit board 400 towards the outer edge 402. Such a configuration has been shown to result in reduced inductance across the entire capacitor array. For example, in some such embodiments, certain sets of the capacitors are configured to cause current to flow radially inward, and others of the sets of capacitors are configured to cause current to flow radially outward, resulting in "counter flows" of current that tend to cancel out or otherwise (e.g., via destructive interference), inductance during use. In some embodiments, portions of the capacitors are coupled to each of a plurality of stackable circuit boards, which may include 2, 3, 4, 5, or more individual boards. Portions of the plurality of capacitors may be coupled to either side—or both sides—of any of the stackable circuit boards. As shown, a stackable circuit board 400 may be circular in shape, and may have a carve out 416 extending inward from outer edge 402 toward the center aperture.

In one embodiment, at least ten (10) planar capacitors in parallel, each having a capacitance of no greater than 100 nanoFarads (nF), are able to provide the repeated large voltage pulse discharges required to generate rapid pulse shockwaves without damage to the capacitors. In other embodiments, a minimum of 15, 20, 25, 30, 35, 40 45, or 50 planar capacitors may be used in parallel. Additionally, according to other embodiments, each capacitor may have a maximum capacitance of 95 nF, 90 nF, 85 nF, 80 nF, 75 nF, 70 nF, 65 nF, 60 nF, 55 nF, or 50 nF. In one embodiment, the capacitors each have a length of between 2 mm and 4 mm, and a width of between 1 mm and 3 mm.

In embodiments in which the capacitors are arranged in sets of capacitors, plurality of capacitors may be arranged in between 2 and 20 sets of capacitors, with the sets connected in parallel (e.g., and the capacitors within each set connected in series). Alternatively, the plurality of capacitors may comprise 2, 5, 10, or 15 sets of capacitors. In some embodiments, each set of capacitors comprises fewer than 50 capacitors, but may alternatively comprise 5, 10, 15, 20, 25, 30, 35, 40, or 45 capacitors per set. In some embodiments, the plurality of capacitors comprises at least 100 capacitors. In some embodiments, the plurality of capacitors are arranged in a circuit having an overall inductance of between 2 nH and 200 nH.

Figure 5E:
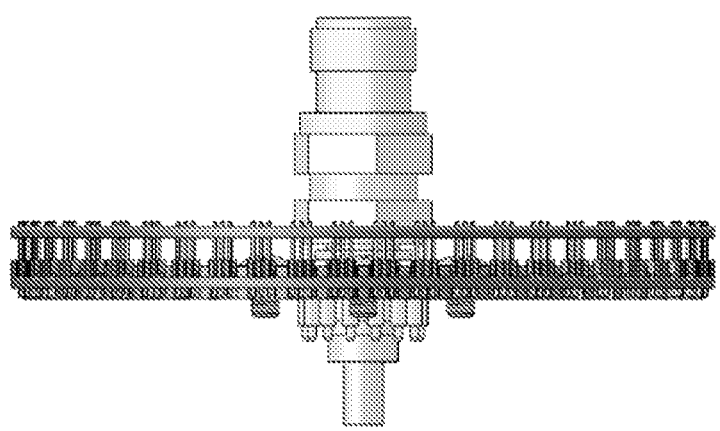
Figure 5D:
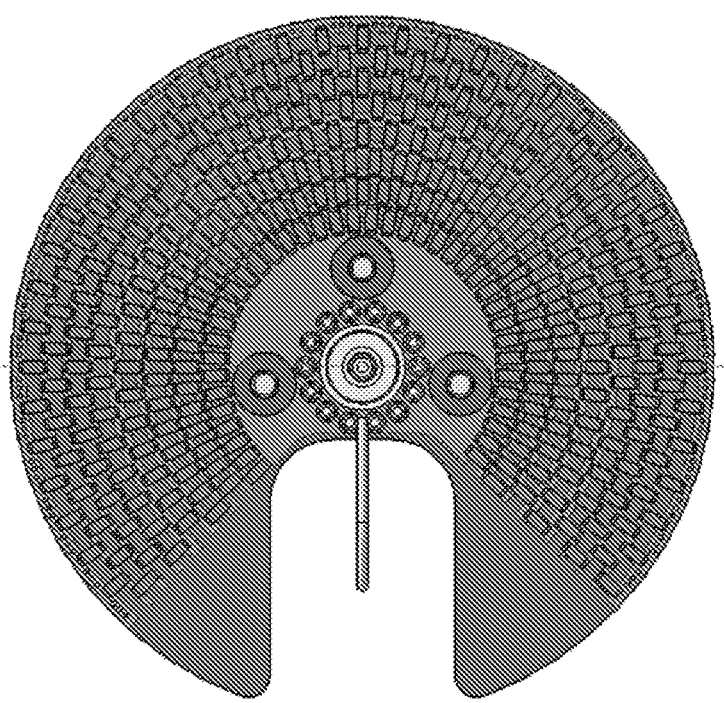
Figure 5C:
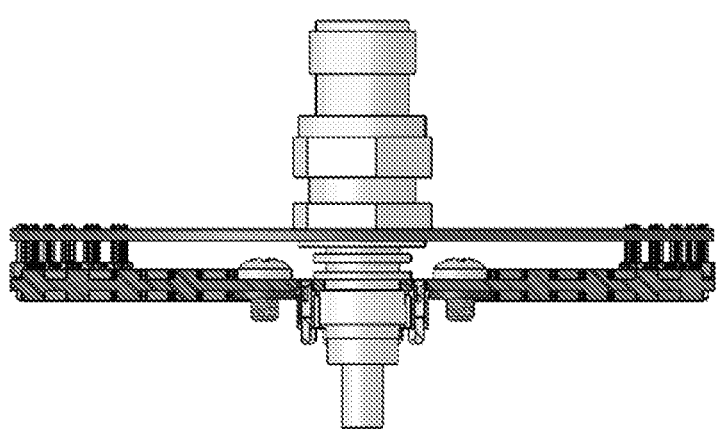

FIGS. 5A-5E depict perspective, cross-sectional, top, and side views of one embodiment of the present assemblies of stackable circuit boards including a capacitor array for use in shockwave pulse generating apparatuses. FIG. 5A depicts a perspective view of one embodiment of the present stackable circuit board assemblies; FIG. 5B depicts another perspective view of the assembly; FIG. 5C depicts a side cross-sectional view of the assembly; FIG. 5D depicts a top view of the assembly; and FIG. 5E depicts a side view of the assembly. As shown, in this embodiment, circuit board 400 is coupled to the second stackable circuit board 500 via connectors 414 such that capacitors 310 of circuit board 400 are electrically connected to second stackable circuit board 500 via the connectors (414). Circuit board 400 is also mechanically coupled to circuit board 500 via a central hub assembly 502. According to this embodiment, Circuit board 500 provides the low-inductance return path from the central pin to the outermost row of capacitors 310.

FIGS. 6A-6D depict perspective, cross-sectional, and exploded perspective views of another embodiment of the present capacitor array for use in the rapid therapeutic shockwave generation apparatuses and methods. FIG. 6A depicts a perspective view of the capacitor array; FIG. 6B depicts a second perspective view of the capacitor array; FIG. 6C depicts a cross-sectional view of the capacitor array; and FIG. 6D depicts an exploded view of the capacitor array. In this embodiment, the plurality of capacitors 310 is placed on a first stacked circuit board 400 and a second stacked circuit board 500, adjacent to a plurality of electrodes wherein the plurality of small capacitors 310 is placed on opposing sides of each stackable circuit board 400, 500 in a low-inductance pattern. The circuit boards 400, 500 are both electrically coupled to each other via board-to-board connectors 414 and mechanically coupled to each other via a central mechanical assembly 502.

In the embodiment shown, locating the plurality of capacitors 310 near the electrodes enables the arc to be discharged completely and quickly. Once the capacitors 310 within the chamber head (as illustrated by the embodiment depicted in FIG. 3) are discharged, the inter-electrode arc ends, minimizing electrode erosion.

In some embodiments, the improved lifetime of the electrodes is the result of the discharge of the plurality of capacitors 310 near the electrodes. Locating the plurality of capacitors 310 near the electrodes in a low inductance pattern provides the capacitor/electrode setup with an overall low inductance. As a result, the plurality of capacitors 310 within the chamber is able to be discharge completely and quickly.

As shown, the central mechanical assembly 502 comprises a contact ring 600, a ring adapter 602, a spacer 604, a replacement pin socket 606, a center pin 608, and a plurality of nuts 610. The ring adapter 602 may have a plurality of teeth 612 that are configured to be inserted into apertures in the second stackable circuit board 500 such that the teeth 612 prevent the second stackable circuit board 500 from rotating independent from the ring adapter 602.

In the embodiment shown, the capacitors may be configured to cause current to flow from the center of the second stackable circuit board 500 towards its outer edge, through the board-to-board connectors 414 to the outer edge of the first stackable circuit board 400 and from there to the center of the first stackable circuit board 400. Each stackable circuit board 400, 500 may have a thickness of between 0.02 and 0.2 inches. Alternatively, the boards 400, 500 may have thicknesses of between 0.03 and 0.125 inches, or between 0.04 and 0.1 inches.

Figures 7A, 7B, 7C:
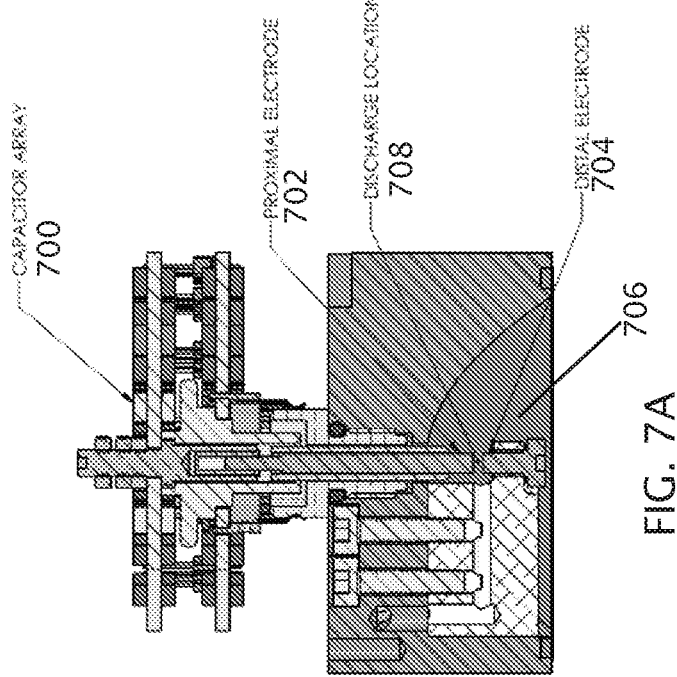
FIGS. 7A-7C depict various views of a capacitor array affixed to a pair of stackable circuit boards coupled to a pair of electrodes in a shock wave generation chamber.

FIGS. 7A-7C depict cross-sectional and side views of one embodiment of the disclosed capacitor array coupled shockwave generation chamber. According to the embodiment as shown in FIG. 7A, the capacitor array 700 is coupled to plurality of electrodes comprising a proximal electrode 702 and a distal electrode 704. In this embodiment, both the proximal electrode 702 and the distal electrode 704 are disposed in a chamber 706, which is configured to be filled with liquid. In at least one embodiment, the chamber 706 is configured to be filled with saline. In yet another embodiment, the chamber 706 is filled with saline. The electrodes 702, 704 are configured to have a short gap between them defining the discharge location 708. The capacitor array 700, along with the coupled electrodes 702, 704 and chamber 706, is configured to perform the two stage discharge approach to shockwave generation. In the first stage, the pulse-generation system is configured to simultaneously: (1) apply voltage pulses to a plurality of electrodes 702, 704 in an electrode chamber 706 such that a portion of a liquid contained within the chamber 706 is vaporized to provide an inter-electrode conductive path in the discharge location 708; and (2) apply voltage pulses to charge a plurality of capacitors located adjacent to the plurality of electrodes 702, 704 in the capacitor array 700. According to this embodiment, in the second stage, the charged plurality of capacitors discharge to generate short inter-electrode arc through the established inter-electrode conductive path in the discharge location 708 resulting in an acoustic shockwave.

In some embodiments, using a two stage pulse discharge approach to generating shock waves results in a short inter-electrode arc times that minimizes electrode erosion, leading to improved electrode lifetime. Electrohydraulic systems that use a single stage pulse discharge approach (for example, where the pulse generation system applies voltage pulses directly to the electrodes to sequentially form the inter-electrode conductive path, and then generate the inter-electrode arc) suffer from long discharge arc times, and therefore significant electrode erosion. This significant electrode erosion leads to an electrohydraulic shockwave apparatus with short electrode lifetime, increasing the time and expenses necessary for maintenance.

Figure 8B:
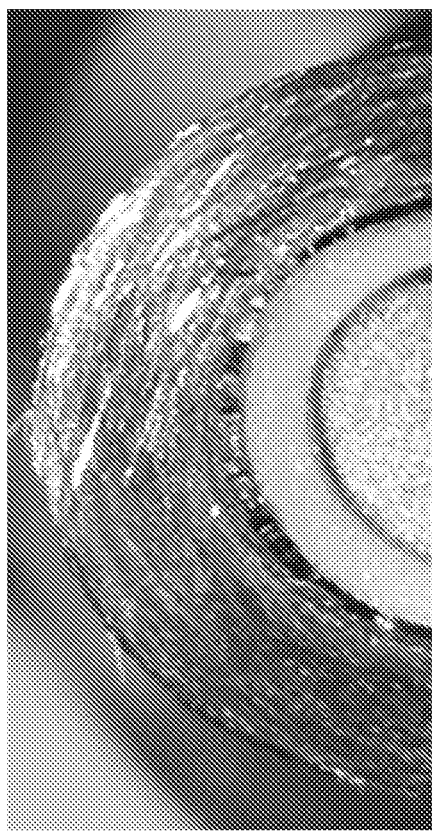
FIGS. 8A and 8B depict the reduced electrode wear resulting from the use of one embodiment of the present apparatus when compared to prior art systems.
Figure 8A:

For example, FIGS. 8A and 8B depict photos comparing an electrode used by a prior art system compared to an electrode implementing the disclosed system. FIG. 8A depicts one embodiment of an electrode run with a prior art pulsed power supply using the single stage approach. In contrast, FIG. 8B depicts an electrode run with one embodiment of the two-stage pulsed generation system disclosed herein. As can be seen by comparing FIGS. 8A and 8B, the electrode run using the prior art pulsed power supply (FIG. 8A) showed significant erosion after less than 100 pulses. Large cratering indicates bulk electrode melt due to extended severe arc duration resulting from the single stage prior art system. Contrary to the electrode implementing the prior art system, the electrode run with the two—stage pulse generation system (FIG. 8B) demonstrated only minimal erosion after 6,200 pulses. The electrode implementing the two-stage system had a wear rate reduction of 15× when compared to that of implementing the prior art system. For example, at equivalent pulse rates, the electrodes depicted in FIG. 8A coupled to a prior art pulse-generation system exhibited a wear rate of approximately 3,750 micro-inches per minute, whereas the electrodes depicted in FIG. 8B coupled to one of the present, inventive two-stage pulse-generation approaches (including a pulse-generation system, and a housing-carried capacitor array), exhibited a wear rate of only 250 micro-inches per minute.

Figure 9:
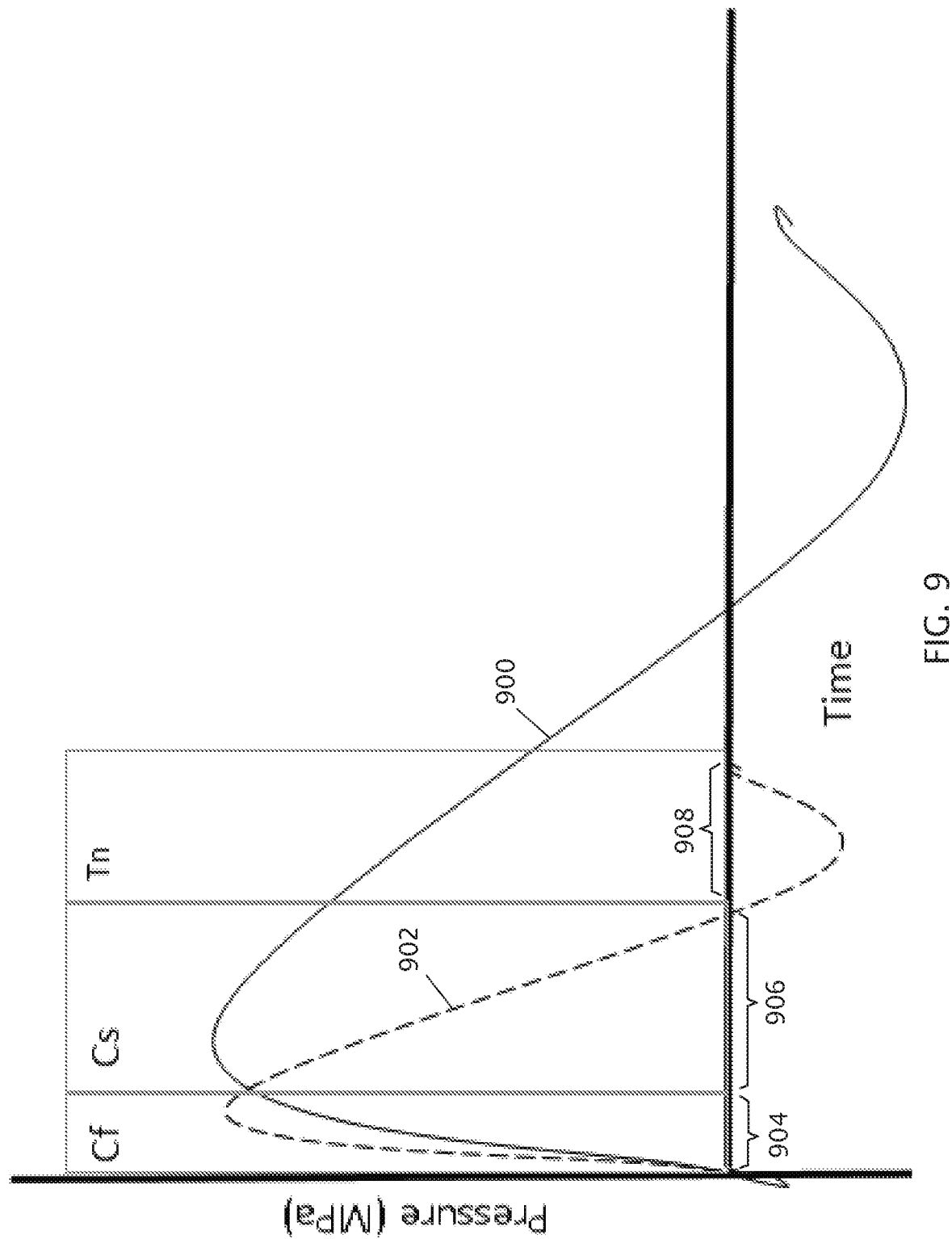
FIG. 9 depicts a graph illustrating a comparison of compressed acoustic wave from an embodiment of the present apparatus and an acoustic wave from a prior art apparatus.
Figure 10:
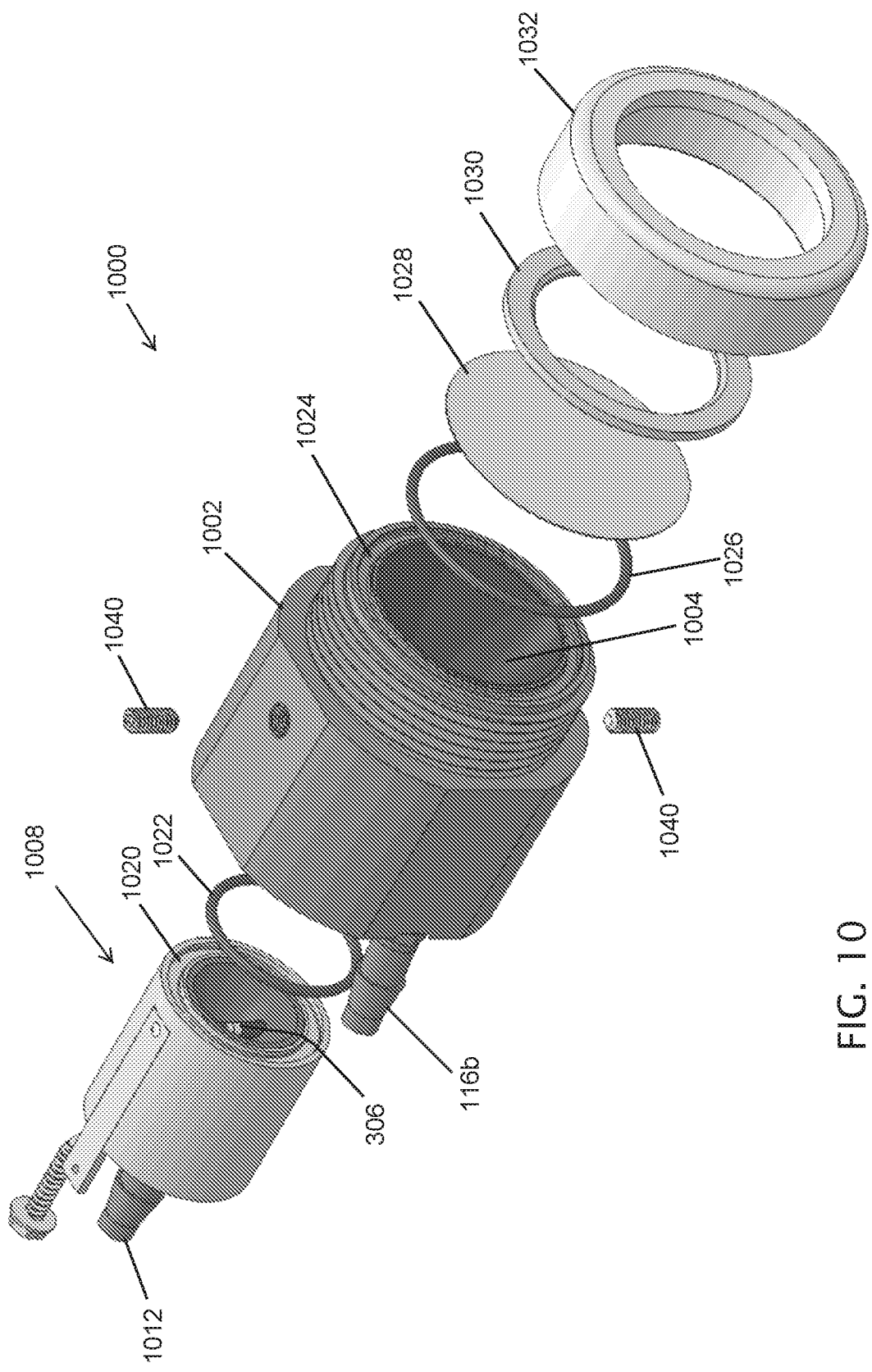
FIG. 10 depicts an exploded perspective view of a further prototyped embodiment of the present probes having a spark head or module.
Figure 12A:
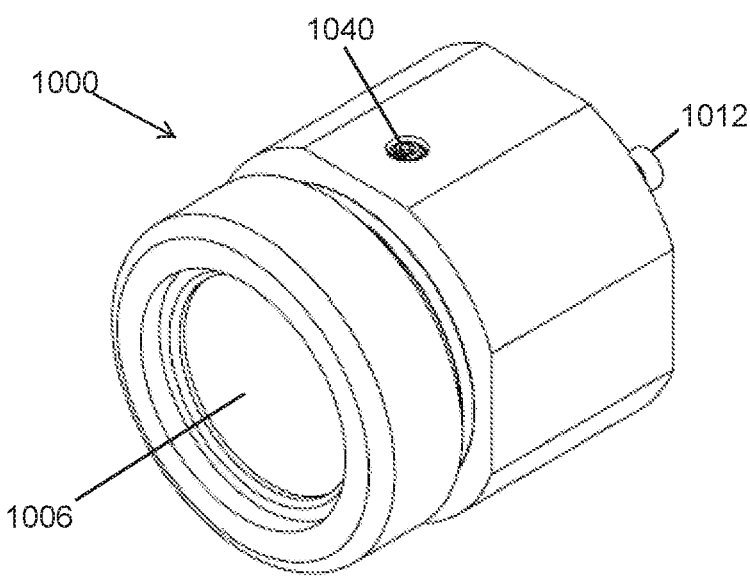
FIGS. 12A and 12B depict perspective and side cross-sectional views, respectively of the probe of FIG. 10.
Figure 12B:
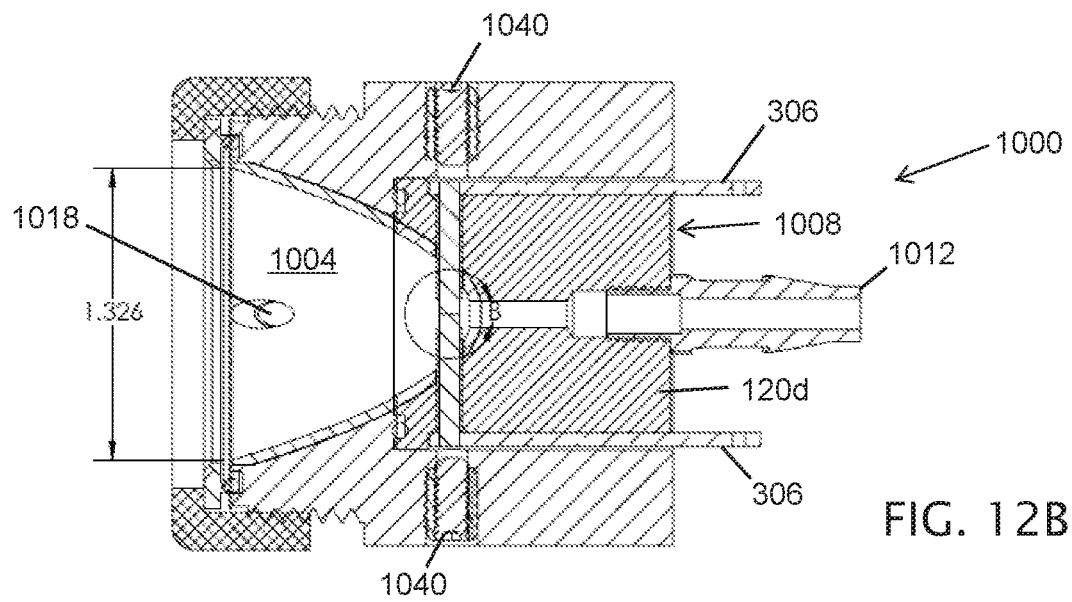
Figure 12C:
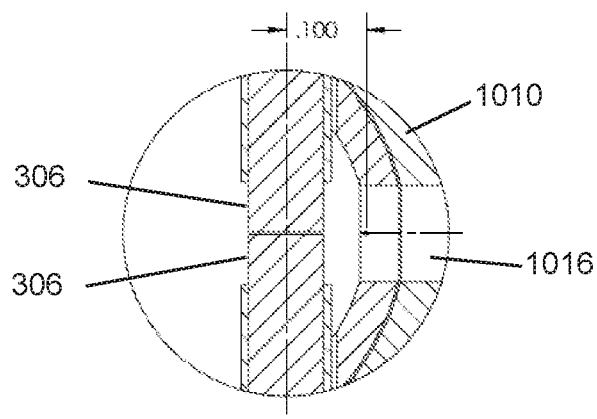
FIG. 12C depicts an enlarged side cross-sectional view of a spark gap of the probe of FIG. 10.

Additionally, according to one embodiment, apparatuses and method for electrohydraulic generation of shockwaves using the two-stage approach disclosed herein generate acoustic waves that are "compressed" when compared to those waves generated by prior art systems. FIG. 9 depicts a graph illustrating the pressure over time of an acoustic wave generated by both the prior art system 900 as well as an acoustic wave generated by the proposed two-stage approach 902. As can be seen from FIG. 9, in comparison to the prior art system, the acoustic wave generated by the two-stage approach has a faster rise acoustic front 904 than that of the prior art approach. More importantly, the long acoustic tail 906 is significantly compressed as a result of the fast capacitor discharge time into an already established inter-electrode conductive path. Finally, the two-stage approach puts more energy into the acoustical pulse and less total energy into the arc when compared to the prior art approach. Less total energy into the arc directly leads to improved electrode life.

Furthermore, the compressed acoustic waves depicted in FIG. 9 are less painful and damaging when applied to tissue. The typical pulse discharge from prior art electrohydraulic systems produce a broad frequency spectrum acoustic wave, typically in the range of 16 Hz to 30 MHz. The long compressive tail 906 of the acoustic wave is composed of the lower frequency spectrum of the acoustic wave. These low frequency components, at the acoustic pressures that are typically used, are the main source of large cavitation bubbles. These large cavitation bubbles, when generated in tissue, result in pain and tissue damage. Due to the short capacitor discharge and the resulting fast arc, the long compressive tail 906 of the acoustic wave is compressed. As a result, large cavitation bubbles secondary to a long tail are minimized.

In one embodiment, the present shockwave generating systems and apparatuses incorporate the probes depicted in FIGS. 10-12C. In this embodiment, probe 1000 comprises: a housing 1002 defining a chamber 1004 and a shockwave outlet 1006; a liquid disposed in chamber 1004; a plurality of electrodes 306 (e.g. in spark head or module 1008) configured to be disposed in the chamber to define one or more spark gaps; and is configured to be coupled to a pulse generation system (300) configured to apply voltage pulses to the electrodes at a rate of between 10 Hz and 5 MHz.

In the embodiment shown, spark head 1008 includes a sidewall or body 1010 and a plurality of electrodes 306 that defined a spark gap. In this embodiment, probe 1000 is configured to permit liquid to be circulated through chamber 1004 via liquid connectors or ports 1012 and 1014, one of which is coupled to the spark head 1008 and the other of which is coupled to housing 1002, as shown. In this embodiment, housing 1002 is configured to receive spark head 1008, as shown, such that housing 1002 and housing 1010 cooperate to define chamber 1004 (e.g., such that spark head 1008 and housing 1002 include a complementary parabolic surfaces that cooperate to define the chamber). In this embodiment, housing 1002 and spark head 1008 includes a channel 1016 (e.g., along a central longitudinal axis of spark head 1008) extending between liquid connector 1012 and chamber 1004 and aligned with the spark gap been electrodes 306 such that circulating water will flow in close proximity and/or through the spark gap. In the embodiment shown, housing 1002 includes a channel 1018 extending between liquid connector 1014 and chamber 1004. In this embodiment, housing 1010 includes a groove 1020 configured to receive a resilient gasket or O-ring 1022 to seal the interface between spark head 1008 and housing 1002, and housing 1002 includes a groove 1024 configured to receive a resilient gasket or O-ring 1026 to seal the interface between housing 1002 and cap member 1028 when cap member 1028 is secured to housing 1002 by ring 1030 and restraining collar 1032.

In the embodiment shown, electrodes 306 each includes a flat bar portion 1034 and a perpendicular cylindrical portion 1036 (e.g., comprising tungsten for durability) in electrical communication (e.g., unitary with) bar portion 1034 such that cylindrical portion 1036 can extend through a corresponding opening 1038 in spark head 1008 into chamber 1004, as shown. In some embodiments, part of the sides of cylindrical portion 1036 can be covered with an electrically insulative and/or resilient material (e.g., shrink wrap) such as, for example, to seal the interface between portion 1036 and housing 1010. In this embodiment, housing 1010 also includes longitudinal grooves 1038 configured to receive bar portions 1034 of electrodes 306. In the embodiment shown, housing 1002 also includes set screws 1040 positioned to align with cylindrical portions 1036 of electrodes 306 when spark head 1008 is disposed in housing 1000, such that set screws 1040 can be tightened to press cylindrical portions 1036 inward to adjust the spark gap between the cylindrical portions of electrodes 306. In some embodiments, spark head 1008 is permanently adhered to housing 1002; however, in other embodiments, spark head 1008 may be removable from housing 1002 such as, for example, to permit replacement of electrodes 306 individually or as part of a new or replacement spark head 1008.

The above specification and examples provide a description of the structure and use of exemplary embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the present devices are not intended to be limited to the particular forms disclosed. Rather, they include all modifications and alternatives within the scope of the claims, and embodiments other than the one shown may include some or all of the features of the depicted embodiment. For example, components may be combined as a unitary structure. Further, where appropriate, aspects of any of the described examples may be combined with aspects of any of the other described examples to form further examples with comparable or different properties and addressing the same or different problems. Similarly, the benefits and advantages described above may relate to one embodiment or may relate to several embodiments.

The claims are not intended to include, and should not be interpreted to include, means-plus- or step-plus-function limitations, unless such a limitation is explicitly recited in a given claim using the phrase(s) "means for" or "step for," respectively.

REFERENCES

The following references, to the extent that they provide exemplary procedural or other details supplementary to those set forth herein, are specifically incorporated herein by reference.

[1] Raymond L. Boxman, Philip J. Martin, David Sanders (1995). *Handbook of Vacuum Arc Science and Technology: Fundamentals and Applications*, Park Ridge, N.J.: Noyes Publications, pp. 316-319
[2] V. Ya. Ushakov, et al. (2007). *Impulse Breakdown of Liquids*, New York, N.Y.: Springer
[3] Schmitz C, et al. Treatment of chronic plantar fasciopathy with extracorporeal shock waves (review). Journal of Orthopaedic Surgery and Research 2013 8:31
[4] U.S. Pat. No. 8,672,721 entitled "High power discharge fuel igniter" by L. Camilli
[5] U.S. Pat. No. 5,245,988 entitled "Preparing a circuit for the production of shockwaves" by W. Einars, et al.
[6] U.S. Pat. No. 4,005,314 entitled "Short pulse generator" by M. Zinn
[7] German Patent No. DE 3150430 C1 entitled "Circuit for generating an underwater discharge" by G. Heine, et al.
[8] U.S. Pat. No. 3,604,641 entitled "Apparatus for hydraulic crushing" by B. R. Donoghue, et al.

The invention claimed is:

1. An apparatus for generating therapeutic shock waves, comprising:
    a housing defining a chamber and a shockwave outlet, the chamber being configured to be filled with a liquid;
    a plurality of electrodes configured to be disposed in the chamber to define one or more spark gaps;
    a plurality of capacitors coupled to one or more circuit boards carried by the housing and in electrical communication with the plurality of electrodes; and
    where the plurality of electrodes is configured to be coupled to a pulse-generation system such that: (i) the housing is movable relative to the pulse-generation system, and (ii) the pulse-generation system is in electrical communication with the plurality of electrodes and the plurality of capacitors such that the plurality of electrodes and the plurality of capacitors can simultaneously receive voltage pulses from the pulse-generation system; and
    where the plurality of capacitors are configured to, upon reaching a threshold charge, discharge to the plurality of electrodes.

2. The apparatus of claim 1, where:
    each of the plurality of capacitors is planar; and
    the pulse-generation system is configured to perform a two stage pulse discharge, the two stage pulse discharge including
        a first stage where the pulse-generation system is configured to apply voltage pulses simultaneously to:
            the plurality of electrodes to begin to vaporize and ionize portions of the liquid to provide at least one inter-electrode conductive path
            between the plurality of electrodes, and the plurality of capacitors to charge the plurality of capacitors; and
        a second stage where the plurality of capacitors are configured to, upon reaching a threshold charge, discharge to the plurality of electrodes to generate one or more arcs along the one or more inter-electrode conductive paths to vaporize additional portions of the liquid and generate one or more acoustic shock waves.

3. The apparatus of claim 1, where:
the one or more circuit boards and the electrode are positioned within the housing;
the plurality of capacitors are arranged in a circuit having an overall inductance of between 2 nH and 200 nH; and
the plurality of capacitors comprises between 2 and 20 sets of capacitors with the sets of capacitors connected in parallel, each set of capacitors comprises 10 or more capacitors in series, or a combination thereof.

4. The apparatus of claim 1, where:
the one or more circuit boards comprise a plurality of stackable circuit board; and
the plurality of capacitors is coupled to the plurality of stackable circuit boards including a first stackable circuit board, and a second stackable circuit board coupled to the first stackable circuit board.

5. The apparatus of claim 4, where a first portion of the plurality of capacitors is coupled to the first stackable circuit board, and a second portion of the plurality of capacitors is coupled to the second stackable circuit board.

6. The apparatus of claim 5, where the first portion of the plurality of capacitors is disposed on a first side of a first stackable circuit board, and the second portion of the plurality of capacitors is disposed on a second side of a second stackable circuit board, and the second side of the second circuit board is opposite the first side of the first stackable circuit board.

7. The apparatus of claim 6, where:
the first portion of the plurality of capacitors is coupled to the first stackable circuit board in a circular pattern;
the second portion of the plurality of capacitors is coupled to the second stackable circuit board in a circular pattern; and
the first stackable circuit board is electrically coupled to the second stackable circuit board by connectors disposed along outer edges of the stackable circuit boards.

8. The apparatus of claim 7, where first portion of the plurality of capacitors is configured to cause current to flow from the outer edge of the first stackable circuit board towards a center of the first stackable circuit board, and the second portion of the plurality of capacitors is configured to cause current to flow from the outer edge of the second stackable circuit board towards a center of the second stackable circuit board.

9. The apparatus of claim 1, where:
the plurality of capacitors comprises at least 100 capacitors,
the plurality of capacitors each have a length of between 2 mm and 4 mm, and a width of between 1 mm and 3 mm,
the one or more circuit boards comprise a plurality of stackable circuit boards each have a thickness of between 0.02 inches and 0.2 inches;
the pulse-generation system is configured to provide an inter-electrode conductive path by applying voltage to charge the plurality of capacitors during a period that the pulse-generation system applies voltage to the plurality of electrodes; and
the plurality of capacitors are configured to, upon reaching the threshold charge, discharge to the plurality of electrodes to generate one or more arcs along the inter-electrode conductive paths to vaporize additional portions of the liquid and generate one or more acoustic shock waves.

10. A capacitor-array apparatus for use in generating therapeutic shock waves, comprising:
one or more circuit boards each circuit board of the one or more circuit boards having a first side and a second side; and
a plurality of first capacitor sets coupled to the one or more circuit boards, each of the first capacitor sets comprising two or more first capacitors connected in series and arranged in a first pattern;
a plurality of second capacitor sets coupled to the one or more circuit boards, each of the second capacitor sets comprising two or more second capacitors connected in series and arranged in a second pattern;
where each of the plurality of first capacitor sets are connected in parallel, and each of the plurality of second capacitor sets are connected in parallel; and
where the one or more circuit boards are configured to be coupled to an electrode such that the electrode is in electrical communication with the first and second capacitor sets; and
where the plurality of first capacitor sets, the plurality of second capacitor sets, and the electrode simultaneously receive voltage pulses via a pulse generation system.

11. The apparatus of claim 10, where at least one of the one or more circuit boards is interposed between one of the first capacitor sets of the first plurality of capacitor sets and one of the second capacitors sets of the second plurality of capacitor sets.

12. The apparatus of claim 10, further comprising:
a housing; and
where the one or more circuit boards and the electrode are positioned within the housing.

13. The apparatus of claim 10, where the one or more circuit boards comprises a plurality of stackable circuit boards, including: a first stackable circuit board and a second stackable circuit board coupled to the first stackable circuit board.

14. The apparatus of claim 13, where the plurality of first capacitor sets is coupled to the first stackable circuit board, and the plurality of second capacitor sets is coupled to the second stackable circuit board.

15. The apparatus of claim 13, where the plurality of first capacitor sets is disposed on the first side of the first stackable circuit board, and the plurality of second capacitor sets is disposed on the second side of the first stackable circuit board, and the second side of the first stackable circuit board is opposite the first side of the first stackable circuit board.

16. The apparatus of claim 14, where:
the plurality of first capacitor sets is coupled to the first stackable circuit board in a circular pattern; and
the plurality of second capacitor sets is coupled to the second stackable circuit board in a circular pattern.

17. The apparatus of claim 16, where the first stackable circuit board further comprises an outer edge and a center, the second stackable circuit board further comprises an outer edge and a center; and the plurality of first capacitor sets is configured to cause current to flow from the outer edge of the first stackable circuit board towards the center of the first stackable circuit board, and the plurality of second capacitor sets is configured to cause current to flow from the outer edge of the second stackable circuit board towards the center of the second stackable circuit board.

18. The apparatus of claim 17, where:
the first stackable circuit board is electrically coupled to the second stackable circuit board by connectors disposed along the outer edges of the stackable circuit boards; and
the electrode is fixed in at least two degrees of freedom relative to the one or more circuit boards.

19. A method of producing a compressed acoustic wave using an apparatus for generating therapeutic shock waves, the method comprising:
applying voltage pulses to a plurality of electrodes in a chamber defined by a housing and filled with liquid such that portions of the liquid begin to vaporize and ionize to provide an inter-electrode conductive path;
applying voltage to a plurality of capacitors coupled to a plurality of stackable circuit boards carried by the housing and in electrical communication with the plurality of electrodes to charge the plurality of capacitors; and
upon the plurality of capacitors reaching a threshold charge, discharging the plurality of capacitors to the electrodes to generate an inter-electrode arc along the established inter-electrode conductive path and thereby generate of at least one acoustic shock wave;
wherein applying voltage to the plurality of electrodes and the plurality of capacitors is performed simultaneously.

20. The method of claim 19, where the voltage pulses applied to the plurality of electrodes is between 500 V and 10,000 V.

* * * * *